(12) United States Patent
Bolland et al.

(10) Patent No.: US 9,180,143 B2
(45) Date of Patent: Nov. 10, 2015

(54) DECELLULARISATION OF TISSUE MATRICES FOR BLADDER IMPLANTATION

(71) Applicant: Tissue Regenix Limited, Leeds (GB)

(72) Inventors: Fiona Bolland, Heslington (GB); Jennifer Southgate, Heslington (GB); Sotirios Korossis, Leeds (GB); Eileen Ingham, Leeds (GB)

(73) Assignee: Tissue Regenix Limited, Leeds (GB)

( * ) Notice: Subject to any disclaimer, the term of this patent is extended or adjusted under 35 U.S.C. 154(b) by 0 days.

(21) Appl. No.: 14/445,710

(22) Filed: Jul. 29, 2014

(65) Prior Publication Data
US 2015/0050359 A1 Feb. 19, 2015

Related U.S. Application Data

(62) Division of application No. 12/295,190, filed as application No. PCT/GB2007/001117 on Mar. 28, 2007, now Pat. No. 8,828,448.

(30) Foreign Application Priority Data

Mar. 29, 2006 (GB) .................................. 0606231.9

(51) Int. Cl.
| C12N 5/00 | (2006.01) |
|---|---|
| A01N 1/00 | (2006.01) |
| A61K 35/22 | (2015.01) |
| A61L 27/36 | (2006.01) |
| A61L 27/38 | (2006.01) |
| A61F 2/04 | (2013.01) |
| G01N 33/50 | (2006.01) |
| C12N 5/073 | (2010.01) |

(52) U.S. Cl.
CPC ............... *A61K 35/22* (2013.01); *A61F 2/042* (2013.01); *A61L 27/3604* (2013.01); *A61L 27/3679* (2013.01); *A61L 27/3687* (2013.01); *A61L 27/38* (2013.01); *C12N 5/0068* (2013.01); *G01N 33/5088* (2013.01); *A61L 2430/00* (2013.01); *A61L 2430/22* (2013.01); *A61L 2430/40* (2013.01); *C12N 5/0605* (2013.01); *C12N 2509/00* (2013.01); *C12N 2533/92* (2013.01)

(58) Field of Classification Search
CPC ............... A61K 35/22; A61L 2430/22; C12N 2509/00; C12N 5/0605
USPC .................................... 424/558, 423; 435/1.1
See application file for complete search history.

(56) References Cited

U.S. PATENT DOCUMENTS

| 4,776,853 A | 10/1988 | Klement et al. |
| 2004/0234507 A1 | 11/2004 | Stone |
| 2005/0043819 A1 | 2/2005 | Schmidt et al. |

FOREIGN PATENT DOCUMENTS

| GB | 2375771 A | 11/2002 |
| WO | WO 96/32905 A1 | 10/1996 |
| WO | WO 99/32049 A1 | 7/1999 |
| WO | WO 01/49827 A1 | 7/2001 |
| WO | WO 01/54619 A1 | 8/2001 |
| WO | WO 02/40630 A2 | 5/2002 |
| WO | WO 02/096476 A1 | 12/2002 |

OTHER PUBLICATIONS

Bolland et al. "Development and characterization of a full-thickness acellular porcine bladder matrix for tissue engineering", *Biomaterials* 28:1061-1070 (2007).
Gilbert et al. "Decellularization of tissues and organs", *Biomaterials* 27:3675-3683 (2006).
International Search Report corresponding to International Application No. PCT/GB2007/001117 mailed Mar. 17, 2008.
Notification Concerning Transmittal of International Preliminary Report on Patentability (Chapter I of The Patent Cooperation Treaty) corresponding to International Application No. PCT/GB2007/001117 mailed Oct. 9, 2008.
Search Report corresponding to International Application No. GB0706014.8 dated May 24, 2007.
Kimuli et al. "In vitro assessment of decellularized porcine dermis as a matrix for urinary tract reconstruction", *BJU International* 94:859-866 (2004).
Zhang et al. "Preliminary research on preparation of porcine bladder acellular matrix graft for tissue engineering applications", *Zhonghua Yi Xue Za Zhi* 85(38):2724-2727 (2005) Abstract Only.
Bolland et al. "Development and characterisation of a full-thickness acellular porcine bladder matrix for tissue engineering", *Biomaterials* 28:1061-1070 (2007).
Search Report corresponding to International Application No. GB0606231.9 dated Jan. 29, 2007.
Search Report corresponding to International Application No. GB0718215.7 dated Nov. 7, 2007.
Brown et al. "22 week assessment of bladder acellular matrix as a bladder augmentation material in a porcine model", *Biomaterials* 23:2179-2190 (2002).
Merguerian et al. "Acellular bladder matrix allografts in the regeneration of functional bladders: evaluation of large-segment (>24 cm$^2$) substitution in a porcine model", *BJU International* 85:894-898 (2000).
Conklin et al. "Development and evaluation of a novel decellularized vascular xenograft", *Medical Eng. & Physics* 24:173-183 (2002).
Kasimir et al. "Comparison of different decellularization procedures of porcine heart valves", *Int. J. Artificial Organs* 26(5):421-427 (2003).
Kasimir et al. "The decellularized porcine heart valve matrix in tissue engineering", *Thromb Haemost* 94:562-567 (2005).
Office Action corresponding to Indian Application No. 9011/delnp/2008 issued Dec. 2, 2014.

*Primary Examiner* — Tekchand Saidha
*Assistant Examiner* — MD. Younus Meah
(74) *Attorney, Agent, or Firm* — Myers Bigel Sibley & Sajovec, P.A.

(57) ABSTRACT

The invention provides an improved method of producing a natural, acellular matrix scaffold for subsequent use in tissue-engineered replacement of tissues such as the bladder. Decellularization is carried out on an expanded or distended bladder and the product retains the strength and compliance of natural material. The invention also provides use of the matrix scaffolds as wound healing material and to investigate tissue structure and function in vitro.

5 Claims, 30 Drawing Sheets

A

B

E

F

DECELLULARISATION OF TISSUE MATRICES FOR BLADDER IMPLANTATION

CROSS REFERENCE TO RELATED APPLICATIONS

This application is a divisional of U.S. patent application Ser. No. 12/295,190, now allowed, filed on Sep. 29, 2008, which claims priority to and is a 35 U.S.C. §371 national phase application of PCT International Application No. PCT/GB2007/001117, having an international filing date of Mar. 28, 2007 and claiming priority to Great Britain Patent Application No. 0606231.9, filed Mar. 29, 2006. The disclosures of each application are incorporated herein by reference in their entireties. The above PCT International Application was published in the English language and has International Publication No. WO 2007/110634A2.

The present invention relates to a method of producing a natural, acellular matrix scaffold for subsequent use in tissue-engineered replacement of tissue. The invention provides a biomaterial that is suitable for tissue replacement and/or repair particularly but not exclusively in the fields of gastroenterology, urology, cosmetic surgery, wound repair and reconstructive surgery. The invention also provides use of the matrix scaffolds to investigate tissue structure and function in vitro.

BACKGROUND

At present, natural biomaterials are predominantly used in reconstructive surgery, mainly in the fields of gastroenterology, urology and wound-healing, but with increasing applications in cardiovascular and cosmetic surgery. One such biomaterial, porcine small intestinal submucosa (SIS), has been used in gastroenterology, urology and wound-healing applications as it is easily incorporated into host tissue and remodeled. However, recent work to investigate the adherence and viability of human cells seeded onto SIS demonstrated that commercially-available SIS specimens contained porcine nuclear residues and was cytotoxic in vitro. In addition, clinical use of SIS has resulted in localised inflammation, suggesting the material can cause an immunological response in vivo. An alternative natural biomaterial is decellularised porcine dermis (Permacol™) which has a wide range of uses in medical and cosmetic procedures and has been implanted in over 8500 patients in over 70 different surgical procedures since being licensed for use in humans in 1998. However, Permacol™ a disadvantage associated with this material is that not only is it only partially resorbable but when it is used in an animal model of bladder augmentation it has been shown to cause micro-calcification and irregular detrusor regeneration. Furthermore, Permacol™ is unable to support in vitro recellularisation thus preventing its use as a biomaterial that could be seeded with cells and functionalised prior to implantation. An improved natural biomaterial that is immunologically inert and able to support recellularisation would offer an immediate advantage in the art.

It is estimated that over 400 million people worldwide suffer from some form of bladder dysfunction. A variety of diverse congenital and acquired conditions result in bladder dysfunction, for example cancer, congenital abnormalities, nerve damage or trauma. Currently, the major surgical solution is surgical reconstruction. It is known in the prior art to repair or augment or replace the bladder during these procedures with vascularised segments of the patient's own tissue derived from their stomach or more commonly their intestine. However, this latter procedure ('enterocystoplasty') is associated with significant clinical complications that arise due to the exposure of the epithelial lining of the intestine to urine. It has been found that the use of intestine results in significant complications, such as infection and development of bladder stones, as the intestine is lined by an absorptive and mucus-secreting epithelium that is incompatible with long-term exposure to urine. Consequently, a number of alternative approaches have been proposed to find a practical and functional substitute for native bladder tissue. One of the alternative solutions is 'composite enterocystoplasty', where the de-epithelialized intestine wall is lined with bladder epithelial cells that have been propagated in vitro, to augmenting the urinary system with natural or synthetic biomaterials that may incorporate in vitro-propagated cells. However even this modified form of enterocystoplasty has been associated with adverse side effects. The lack of an entirely satisfactory clinical procedure has led researchers to investigate alternative strategies.

Attempts have been made to develop suitable biomaterials for urological tissue engineering using both synthetic materials, for example polyglycolic acid and poly L-lactic acid, and naturally derived materials including SIS, Permacol™ and porcine bladder matrix. However none of these materials have been found to be totally successful vis a vis immunogenicity and rejection and recellularisation.

Tissue matrices prior to implantation undergo a process of decellularisation in order to reduce their immunogenicity once implanted. This process involves removing the donor cells, whilst ideally retaining the biomechanical structure and function of the matrix. As regards the bladder, it is especially desirable to maintain the normal mechanical properties and its elasticity.

A problem associated with the use of a bladder matrix is that bladder tissue is relatively thick (1-5 mm when not distended). This in turn means that it is difficult to decellularise bladder tissue to provide an immunologically inert scaffold matrix using routine methods known in the art. Attempts to decellularise dissected segments of full thickness porcine bladder have resulted in incomplete decellularisation. Histological analysis of these samples indicated that cells had not been removed from the muscular bladder wall. In its retrieved form, the porcine bladder was too thick to allow efficient penetration of the solutions used throughout the decellularisation process. In order to overcome this problem segments of bladder tissue of reduced thickness could be used to enable successful decellularisation.

An improved method of decellularisation that could be used to decellularise whole bladders or other membranous sacs of full thickness, whilst retaining the biomechanical properties of the tissue, would offer immediate advantage in the field of particularly but not exclusively, urological tissue engineering.

BRIEF SUMMARY OF THE DISCLOSURE

According to a first aspect of the invention there is provided a method of decellularisation of a tissue comprising a distensible membranous sac, the method comprising:
(i) immersing the distensible membranous sac in a buffer solution at a mild alkaline pH which includes active amounts of a proteolytic inhibitor;
(ii) distending the distensible membranous sac by introducing a sufficient volume of the same buffer solution into the interior cavity of the sac and;
(iii) continuing decellularisation of the sac by replacing and introducing fresh solutions both around the exterior surface of the sac and into the sac interior itself so as to maintain distension of the sac during decellularisation.

It will be appreciated that step (ii) may be performed prior to step (i) and that the essence of these two steps is to ensure that both the inside and outside of the distensible membranous sac is in contact with the buffer for effective decellularisation to take place. Whether the sac is fluid filled with the buffer and then immersed in the buffer or whether it is immersed in the buffer and then filled with the buffer is not material to the method providing that the sac is in contact with the buffer on both its inner and outer membranous surfaces and that it remains in a distended form whilst decellularisation occurs.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Reference herein to a distensible membranous sac is intended to include a tissue or sac or balloon of tissue that has an elastic or flexible membrane. That is to say tissue when in vivo has the ability to expand and to return to a normal resting state without rupture or disruption of its mechanical properties.

Reference herein to decellularisation is intended to include the removal of cellular membranes, nucleic acids, lipids, cytosolic components and retaining an ECM having as major components collagens and elastins.

Preferably, the distensible membranous sac is clamped before and after each step of fluid replacement so as to prevent fluid loss and to maintain distension of the sac.

Preferably, the fluid volume added to the interior cavity of the sac at each step is in the region of 250-750 ml and more preferably in the region of 350-650 ml and more preferably still is about 500 ml. The volume selected is dependent on the size of the distensible sac and may vary accordingly, the volume introduced into the sac is sufficient to maintain distension throughout the decellularisation process.

Preferably, the fluid volume around the exterior of the sac is sufficient to cover the whole of the distended fluid filled sac. It is convenient whilst refreshing the fluid inside the sac to simultaneously replace the fluid surrounding the exterior of the sac.

Once the process of decellularisation is complete the distensible sac may be dissected to form a flattened sheet or it may remain intact as a sac depending on its intended subsequent use.

The bladder is an extremely compliant organ and is able to expand to more than 15 times its contracted volume, it this property that has been exploited in the method of the present invention. By distending the intact bladder to stretch and thin the bladder wall, solutions were able to permeate throughout the thinned wall, resulting in complete decellularisation whilst surprisingly retaining properties of native bladder tissue.

Preferably, the distensible membranous sac is a whole bladder.

Preferably, the distensible membranous sac is derived from a pig.

However, it will be appreciated that the method of the present invention is equally applicable a membranous sac derived from a human or any other animal that has physical parameters, for example size, that are compatible with a human bladder. Thus the method of the invention may be used to decellularise donor human bladders. It may also be used to, for example, replace the bladder from another animal such as a cat with a membranous sac derived from a cat or another species which has approximately the same size as a cat's bladder. The interspecies cross is not intended to limit the scope of the invention.

Porcine whole bladder is the particularly preferred tissue for use in the method of the present invention since not only is there a ready supply but its size, physical and mechanical characteristics are similar to humans which makes it compatible as a human bladder tissue replacement.

Preferably, the method of decellularisation of a tissue comprising a distensible membranous sac, comprises:
(i) distending the distensible membranous sac by introducing a sufficient volume of a buffer solution at a mild alkaline pH which includes active amounts of a proteolytic inhibitor into the sac whilst simultaneously immersing the sac in the same buffer solution;
(ii) removing said buffer from both the interior cavity of the sac and the surrounding exterior area and replacing it with an anionic detergent at a mild alkaline pH at a concentration which is sufficient to effect decellularisation but which maintains the histoarchitecture of the biological material;
(iii) removing said detergent from the interior of the sac and its exterior and replacing it with a washing buffer solution at a mild alkaline pH both with and without active amounts of proteolytic inhibitors so as to wash both the interior and exterior surfaces of the distensible membranous sac;
(iv) removing said washing buffer from both the interior of the sac and its exterior and replacing it with a solution comprising one or more enzymes selected from the group comprising DNase Type I, DNase Type II, and/or Rnase and optionally;
(v) removing the solution comprising one or more enzymes from the interior of the sac and its exterior and optionally placing the biological material in a cryoprotectant medium or storage medium or other suitable protective medium for later use.

Preferably, the method further includes the step of modifying the decellularised matrix with a suitable agent to enhance immunoacceptability of the matrix on implantation. For example and without limitation, the tissue matrix may be treated enzymatically with α-galactosidase or a glycosidase digestion to remove α-gal epitopes (Gal α1-3 Gal β1-4Glc NAC-R). Alternatively, it may be treated chemically with cross-linking agents such as glutaraldehyde or other aliphatic and aromatic diamine compounds that provide additional cross-linking through side chain groups of aspartic and glutamic acid residues of the collagen peptide. It will be appreciated that any suitable agent that is capable of enhancing immunoacceptability and thus reducing the likelihood of post implantation rejection and/or inflammation will be applicable for use in the method of the present invention.

Preferably, the method further includes the step of recellularisation. Recellularisation can be either in vitro or in vivo and may be enhanced by a suitable agent appropriately administered either in vitro or in vivo. The agent may also be coated directly onto the tissue matrix prior to implantation to encourage recellularisation.

As regards the solutions and concentrations of components in the method of the invention, preferably the buffer solution is hypotonic or isotonic. It will be appreciated that each may be used either as the sole buffer or in combination at different stages of the method and that use of hypotonic or isotonic buffer is not intended to limit the scope of the present application.

Preferably, the proteolytic inhibitors are ethylene diamine tetraacetic acid (EDTA) and Aprotinin. We have found Aprotinin particularly effective as a proteolytic inhibitor and of particular utility because of its low toxicity, stability in solution at different pHs and stability at a variety of different temperatures.

Typically, EDTA is used at a concentration range of 1 to 100 mM or 0.01-1.0% (w/v) and typically at 10 mM or 0.1% and Aprotinin at a concentration range of 1-100 KIU and typically at 10 KIU.

Preferably, the mild alkaline conditions of step (i) are in the range of pH above 7.0 and up to pH 10.0, and more preferably are at pH 8.0.

Preferably, the incubation period of step (i) of the method is for between 8 to 24 hours and more preferably is for 14 hours.

Preferably, the anionic detergent is sodium dodecyl sulphate (SDS) or sodium deoxycholate.

Preferably, SDS is used at a concentration equal to or below 0.1% (w/v), and equal to or above 0.03% (w/v).

Reference herein to the term % (w/v) refers to the percentage in weight (grams) per unit volume (100 ml), thus 0.1% w/v is equivalent to 0.1 gm dissolved in 100 ml.

Preferably, sodium deoxycholate is used at a concentration equal to or below 2.0% (w/v) and equal to or above 0.5% (w/v).

Preferably, the incubation period of step (ii) of the method is for between 20 to 28 hours and more preferably is for 24 hours.

Preferably, the mild alkaline conditions of step (ii) are in the range of pH above 7.0 and up to pH 10.0, and more preferably are at pH 8.0.

Preferably, the washing step (iii) of the method involves multiple washes, typically ×3 washes with physiological buffered saline (preferably phosphate buffered saline PBS, 0.01M phosphate buffer, 0.137M NaCl) containing protease inhibitors (0.1% EDTA and 10 KIU/ml Aprotinin), and further, multiple washes, typically ×3 washes with physiological buffered saline without the protease inhibitors.

Preferably, the mild alkaline conditions of step (iii) are in the range of pH above 7.0 and up to pH 10.0, and more preferably are at pH 8.0.

Preferably, the incubation step (iv) of the method is for 4-6 hours at temperature range of between 20° C. to 45° C. and preferably at 37° C.

The DNase Type I, DNase Type II or Rnase are employed in an amount effective so as to eliminate nucleic acids and provide a tissue matrix of limited calcification potential. Accordingly any other agents which are capable of the same function are included within the scope of the present invention.

Preferably, DNAse I is used at a concentration range of 5.0-100 µg/ml and typically at 20 µg/ml and RNAse A at a concentration range of 0.1-10 µg/ml and typically at 1 µg/ml.

The decellularisation process includes osmotic lysis of the cells, solubilisation of cell fragments using SDS, protease inhibitors to inhibit autolysis and nucleases to digest nuclear materials. All stages of the process are carried out using a whole, full thickness distensible sac that is substantially distended during all steps so that its walls are stretched and thinned so allow solutions to permeate throughout the thinned wall, resulting in complete decellularisation thereof.

The method of the present invention provides a process whereby intact whole porcine bladders are distended in a series of decellularisation solutions such that decellularisation of the full thickness bladder wall is achieved. Moreover, the resultant biomaterial retained the physical and structural features of the native bladder tissue and contained no residual cell or nuclear bodies. Results have shown that the underlying bladder histoarchitecture was retained and that the biomaterial produced by the method of the invention when compared to fresh porcine bladder tissue showed no differences in the overall compliance; ultimate tensile strength or ability of the decellularised matrix to retain sutures under force. Furthermore, the bladder biomaterial was biocompatible with cells, as homologous smooth muscle cells were able to repopulate the matrix after 21 days in culture.

Our results have shown there was no significant difference in the ultimate tensile strength of the distensible sac following decellularisation and in terms of its potential applications in vivo, there was no significant difference in the ability of the decellularised matrix to retain sutures under force compared to fresh bladder tissue.

According to a further aspect of the invention there is provided a natural biomaterial product comprising bladder tissue having a DNA content of less than 0.2 µg/mg dry weight, a suture retention strength (Fmax) of between 3-6 N, ultimate tensile strength (apex to base) of between 1-4 MPa, failure strength (apex to base) of between 70-150%.

Preferably, the natural biomaterial product is a whole bladder or is a patch or portion of bladder tissue. It will be appreciated that the natural biomaterial produced by the method of the present inventions retains the above characteristics and parameters and as such may be used either as the whole bladder for transplantation or experimental purposes alternatively patches or portions of the bladder may be used for any of the various surgical uses and scenarios as hereinbefore mentioned.

The biocompatible implant material produced by the method of the present invention is characterised by a DNA content of less than 0.2 µg/mg dry weight, that is to say it is substantially decellularised. It is also characterised by a suture retention strength (Fmax) of between 3-6 N, ultimate tensile strength (apex to base) of between 1-4 MPa, failure strength (apex to base) of between 70-150% all of these parameters indicate that the mechanical strength of the biomaterial product is comparable to natural bladder that has not undergone a decellularisation process according to the method of the invention.

The biomaterial of the present invention is stable, non-cytotoxic and retains the strength and compliance properties of the native bladder, indicating potential use in a range of surgical procedures and as a scaffold for bladder tissue-engineering.

According to a yet further aspect of the invention there is provided a tissue matrix obtainable by the method of the present invention for use as a transplant tissue.

According to a yet further aspect of the invention there is provided use of a tissue matrix obtainable by the method of the present invention as a transplant tissue.

Preferably, the tissue matrix is a bladder tissue matrix.

Preferably, the bladder tissue matrix is used for reconstructive surgery and in particularly in reconstruction surgery of congenital or acquired bladder defects or bladder augmentation.

Initial studies in vitro using alternative biomaterials have proved encouraging in so far as normal urothelial cells (NUC) have been shown to readily attached and grow as a monolayer on the surface of Permacol™, however smooth muscle (SM) cells could only survive when co-cultured with NUC (Kimuli et al BJU Int. 94, 859, 2004) and even when co-cultured with NUC cells the SM cells could not infiltrate the Permacol™. These observations confirm similar finding with SIS matrices and NUC and SM cells (Zhang et al J Urol, 928, 164, 2000). A functionally normal urinary bladder distends passively as it fills with urine, and contracts voluntarily to void. To carry out this normal function the bladder requires a normal SM cell component. We have found that the tissue matrices produced by the present invention could sustain SM cell proliferation, thus making it a suitable biomaterial for urological tissue engineering. Thus the improved method of decellularisation provided in the present invention shows that distensible sacs treated with the method can, when implanted sustain two of the essential cell types vital for normal function.

According to a yet further aspect of the invention there is provided a tissue matrix obtainable by the method of the present invention for use in tissue repair.

According to a yet further aspect of the invention there is provided use of a of a tissue matrix obtainable by the method of the present invention in tissue repair.

It is envisaged that the processed bladder biomaterial will have uses in tissue repair of for example and without limitation as pubovaginal slings and in vaginal repair. It is also envisaged that the bladder biomaterial obtainable by the method of the present invention and having the unique characteristics as hereinbefore described has potential applications in gastroenterology including the repair of abdominal wall defects, such as those caused by trauma, tumour resection, and also in chest wall repair as pericardial patches following tumour excision and could potentially be used for cardiac repair.

According to a yet further aspect of the invention there is provided a tissue matrix obtainable by the method of the present invention for use as in wound healing or wound repair.

According to a yet further aspect of the invention there is provided use of a of a tissue matrix obtainable by the method of the present invention as wound healing or repair material.

Preferably, the processed bladder biomaterial is in the form of a sheet or patch.

In wound care, natural biomaterials can be used in the repair of defects occurring as a result of burns, venous ulcers, diabetic ulcers and large full-thickness defects such as those occurring following acute injury.

According to a, yet further aspect of the invention there is provided a tissue matrix obtainable by the method of the present invention for use as in cosmetic surgery as augmentation material According to a yet further aspect of the invention there is provided use of a of a tissue matrix obtainable by the method of the present invention in cosmetic surgery as augmentation material.

Cosmetic applications for the processed bladder biomaterial include eyebrow augmentation, repair of nasal septum, cleft palate repair, breast surgery, lip, cheek and chin augmentation.

The compliance the biomaterial we have developed also makes it a suitable material for soft and connective tissue coverage, where intimate contact between the matrix and wound surface is required. A custom made patch could be fashioned to fit to the margins of ulcers or wounds with the confidence that it would lie against deep structures in order to protect and encourage healing. This may be of particular benefit in traumatic tissue loss where myocutaneous flaps are currently used to cover exposed bony or tendonous structures. The ability of our biomaterial to conform to underlying structures would make it ideal for augmentation cystoplasty, urothelial coverage in detrusor myectomy and other urological reconstructive procedures.

According to a yet further aspect of the invention there is provided a tissue matrix obtainable by the method of the present invention for use as a scaffold for tissue-engineering.

According to a yet further aspect of the invention there is provided use of a tissue matrix obtainable by the method of the present invention as a scaffold for tissue-engineering.

According to a yet further aspect of the invention there is provided a tissue matrix obtainable by the method of the present invention for use as an in vitro model to investigate bladder function.

According to a yet further aspect of the invention there is provided use of a tissue matrix produced by the method of the present invention as an in vitro model to investigate bladder function.

According to a yet further aspect of the invention there is provided a method of implantation of a tissue matrix in bladder reconstruction or replacement surgery comprising:
 (i) immersing the distensible membranous sac in a buffer solution at a mild alkaline pH which includes active amounts of a proteolytic inhibitor;
 (ii) distending the distensible membranous sac by introducing a sufficient volume of the same buffer solution into the interior cavity of the sac and;
 (iii) continuing decellularisation of the sac by replacing and introducing fresh solutions both around the exterior surface of the sac and into the sac interior itself so as to maintain distension of the sac during recellularisation and;
 (iv) implanting either the whole decellularised distensible sac or a portion thereof into a donor As previously mentioned steps (i) and (ii) may be reversed.

According to a yet further aspect of the invention there is provided a method of wound healing and/or tissue repair comprising:
 (i) immersing the distensible membranous sac in a buffer solution at a mild alkaline pH which includes active amounts of a proteolytic inhibitor;
 (ii) distending the distensible membranous sac by introducing a sufficient volume of the same buffer solution into the interior cavity of the sac;
 (iii) continuing decellularisation of the sac by replacing and introducing fresh solutions both around the exterior surface of the sac and into the sac interior itself so as to maintain distension of the sac during recellularisation and;
 (iv) placing a portion or patch of the decellularised sac onto or around a wound or attaching said portion or patch on or about the tissue to be repaired.

Preferably, any of the further aspects of the invention further include any one or more of the features recited in the first aspect of the invention.

The method of the present invention, products produced thereby and the use of the products provide a decellularised, biocompatible bladder matrix which retains properties of native bladder tissue.

It is envisaged that the acellular matrix retaining the major structural components and strength of the urinary bladder can be used to produce a functional, tissue-engineered construct for use in bladder repair and as an in vitro model to study host cell-matrix interactions and the role of mechanical forces on bladder tissue functionality.

Surgeons who have felt the bladder biomaterial obtainable by the method of the present invention have reported that the strength, feel, compliance and elasticity of the material makes it particularly well suited for any surgical procedures where Permacol™ and other natural biomaterials are being used currently. Indeed it has been indicated that the compliance of the material of the present invention makes it a more attractive material to use than available prior art materials.

Furthermore experimental evidence suggests that decellularised bladder material has a good shelf life even after as long as 30 months storage.

DETAILED DESCRIPTION

Specimen Procurement

Figure 1:
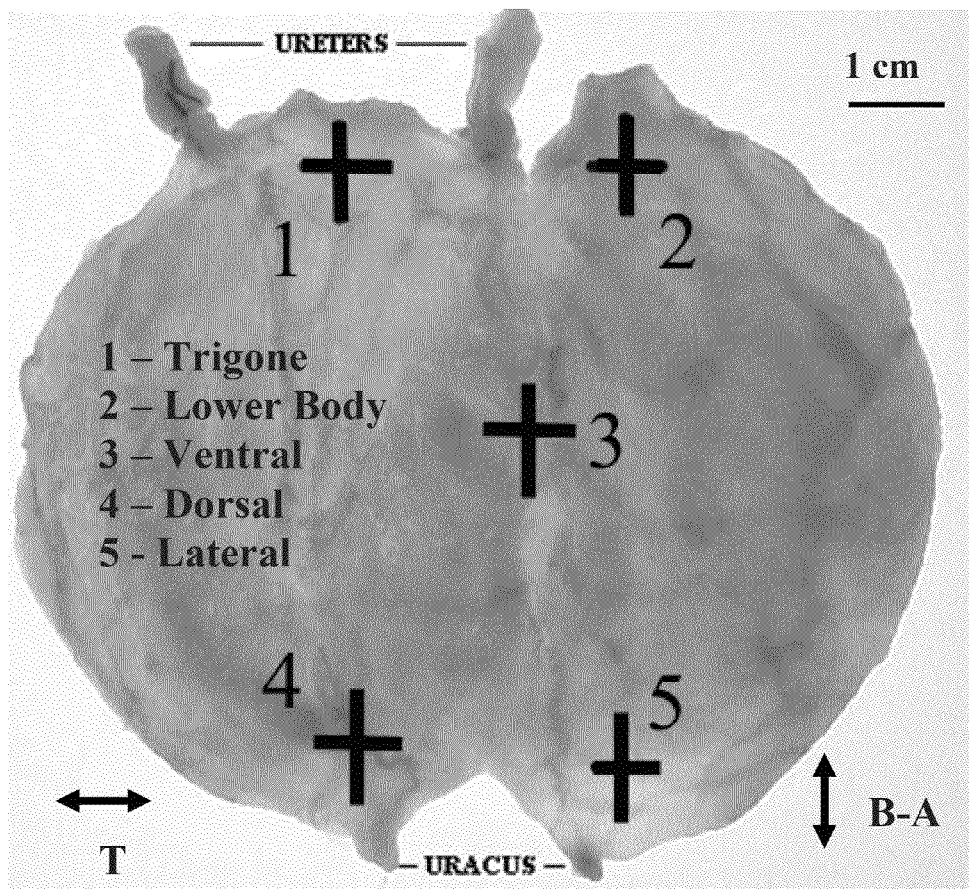
FIG. 1 shows a photomicrograph of dissected bladder showing the five anatomical regions of the bladder that underwent biomechanical characterisation. Tissue strips from all regions were collected in both transverse (T) and base-to-apex (B-A) directions.

Whole porcine bladders were obtained from a local abattoir within 4 h of slaughter and transported to the laboratory on ice in sterile transport medium (Hanks' balanced salt solution (HBSS) containing 10 mM HEPES pH 7.6 and 10 KIU/ml Aprotinin (Trasylol, Bayer, Berkshire, UK).

Porcine Bladder Decellularisation

Intact bladders were washed in phosphate buffered saline (PBS) containing 0.1% w/v ethylene diamine tetra-acetic acid (EDTA) and Aprotinin (10 KIU/ml) to inhibit protease activity. Subsequent treatments, unless otherwise stated, were all carried out with protease inhibition. At each stage the intact bladder was distended with up to 500 ml buffer through a funnel inserted into the bladder neck, closed with Nalgene™ forceps (VWR International Ltd, Poole, UK) and immersed in the same solution. The bladders were decellularised by incubating the bladder for 24 h at 4° C. in hypotonic Tris buffer (10 mM Tris, pH 8.0) followed by distension and incubation with agitation on an orbital shaker for 24 h in 0.1% (w/v) sodium dodecyl sulphate (SDS) in hypotonic Tris buffer at room temperature. Bladders were washed in PBS without protease inhibition, before being incubated for 24 h in 50 U·ml$^{-1}$ deoxyribonuclease I (Sigma, Poole, UK) and 1 Uml$^{-1}$ ribonuclease A (Sigma, Poole, UK) in 10 mM Tris-HCl pH 7.5 with gentle agitation at 37° C. Bladders were sterilized by incubation in 0.1% (v/v) peracetic acid in PBS for 3 h and finally, were washed in sterile PBS once for 24 h followed by 3 periods of 1 h under aseptic conditions. The resulting material was stored in PBS at 4° C. for at least 6 months with no change in appearance or handling.

Histology and Microscopy

Fresh and decellularised tissue samples were fixed in 10% (v/v) neutral buffered formalin, dehydrated and embedded in paraffin wax. Haematoxylin and eosin staining was used to evaluate the cellular content and general histoarchitecture of the porcine bladders. Miller's elastin staining was used to evaluate the elastin content and the Van Gieson technique was used for the identification of collagen I fibres (Bancroft and Stevens, Theory and Practise of Histological Techniques. London, Churchill Livingstone, 1990).

Immuno-labelling of specific proteins was performed using an indirect immunoperoxidase method as previously described (Booth et al, Labinvestigation 76, 843, 1997). Tris-buffered saline [(TBS), 0.05M Tris-HCl, 0.15M NaCl, pH 7.6] was used as the diluent and wash buffer throughout. Non-specific background staining was eliminated by blocking with 10% (v/v) rabbit serum. Monoclonal antibodies were obtained against collagen type I (COL 1), smooth muscle actin (1A4), laminin (LAM89) (Sigma, Poole, UK), collagen type IV (cIV22), vimentin (V9) and desmin (D33) (Dako, High Wycombe, UK). Sections were incubated sequentially in primary antibody for 1 h, biotinylated rabbit ant-mouse Ig (F(ab')2 fragments (Dako, High Wycombe, UK) for 30 min and strepavidin/HRP ABC complex (Dako, High Wycombe, UK) for 30 min, with washing between each step. Bound antibody was visualized using a 3,3'-diaminobenzidene substrate (DAB) reaction catalysed by $H_2O_2$. Sections were counterstained with haematoxylin, before being dehydrated, cleared and mounted in DPX (Sigma, Poole, UK). Omission of the primary antibody from the labelling protocol and the use of irrelevant primary antibodies served as negative controls.

Biochemical Analysis

Three porcine bladders were decellularised for biochemical analysis and comparison with six fresh, untreated porcine bladders. Unless otherwise stated, test solutions for analysis were prepared from samples of fresh and decellularised matrix that had been freeze-dried to constant weight, hydrolysed by incubation with 6M HCl for 4 hours at 120° C. and neutralised to pH 7 with NaOH.

Glycosaminoglycan Assay

The amount of sulphated sugars (GAGs) was determined by dimethylmethylene blue binding (Enobakhare et al, Anal. Biochem. 243, 189, 1996; Farndale et al, Biochim. Biophys, Acta., 883, 173, 1986). Briefly, test solutions were incubated with the dimethylmethylene blue solution and the absorbance read at 525 nm. The amount of GAGs was calculated by interpolation from a standard curve prepared using chondroitin sulphate and phosphate assay buffer (0.1M sodium di-hydrogen orthophosphate, 0.1M di-sodium hydrogen orthophosphate, pH6.8) over a range of concentrations.

Hydroxyproline Assay

The amount of hydroxyproline was determined using a method based on that described elsewhere (Brown et al, Biotechniques 30, 38, 2001; Edwards et al, Clin Chem Acta 104, 161, 1980; Stegemann and Stadler Clin Chem Acta, 18, 267, 1967). A range of hydroxyproline standards were prepared using trans-4-hydroxy-L-proline in hydroxyproline assay buffer [0.17M citric acid, 0.8% (v/v) acetic acid, 0.6M sodium acetate, 0.57M sodium hydroxide and 20% (v/v) propan-1-ol pH6]. 50 µl of each standard and test solution was aliquoted into a clear flat bottomed 96 well plate. Oxidation was achieved by adding 100 µl of chloramine T solution to each well. The plate was gently shaken for five minutes and 100 µl of Ehrlich's reagent added. The plate was covered and incubated at 60° C. for 45 minutes, before reading the absorbance at 570 nm. A standard curve of hydroxyproline concentrations was plotted using the standard solutions and the amount of hydroxyproline present in the test samples determined. To measure the amount of denatured hydroxyproline, fresh and decellularised tissue samples that had been freeze-dried to constant weight were digested with α-chymotrypsin prior to analysis (Bank et al, Matrix Biol. 16, 233, 1997).

DNA Assay

Fresh and decellularised tissue samples that had been freeze-dried to constant weight were digested in papain buffer at 60° C. for 24 hours as previously described (Kim et al Anal Biochem, 174, 168, 1988; Labarca et al Anal Biochem, 102, 344 1980). Test solutions were incubated with Hoechst 33258 dye solution and using a fluorometer, the plate was read using excitation at 365 nm and emission at 458 nm. The amount of DNA was calculated by interpolation from a standard curve prepared using calf thymus DNA solubilised in Tris buffered saline pH 7.6 over a range of concentrations.

Example 1

The bladder wall is composed primarily of collagen, elastin, and smooth muscle and is organised in two major layers: the lamina propria and the detrusor. The lamina propria consists of the urothelium, which lines the luminal surface, and an underlying connective tissue matrix that contains a dense layer of randomly oriented collagen fibres in which the capillary network of the bladder is embedded. The majority of the lamina propria is constituted by a thick layer of collagen that functions to maintain the shape of the bladder wall and to limit its overall compliance (ratio of maximum volume divided by pressure). The detrusor muscle layer provides the contraction during voiding, and is composed of muscle fibres of 50 to 150 µm in diameter, and 20-50 µm apart and interconnected with collagen bundles. Histological analysis of the decellularised matrix showed that whilst the urothelium and smooth muscle cells had been removed, the underlying histoarchitecture was retained. (See FIGS. 2 and 3 and Example 6)

Example 2

Glycosaminoglycans (GAGs) are the main component of the ground substance in which cells, collagen (comprised of hydroxyproline, proline and glycine) and elastin fibres are embedded. Compared to fresh bladder tissue, the proportion of hydroxyproline and GAGs in decellularised tissue samples relative to total dry weight, was significantly higher due to the loss of other soluble proteins and cell components (Table 1). Table 1 below shows the biochemical characterisation of fresh and decellularised porcine bladder tissue.

TABLE 1

| Component | Amount (µg/mg dry weight) | |
|---|---|---|
| | Fresh bladder tissue | Decellularised bladder tissue |
| Total protein | 345 (+/−20.4) | 133.3 (+/−7.6)* |
| DNA | 2.8 (+/−0.1) | 0.1 (+/−0.1)* |
| Hydroxyproline | 46.8 (+/−2.0) | 82.0 (+/−4.3)* |
| Denatured Hydroxyproline | 2.0 (+/−0.1) | 0.7 (+/−0.1)* |
| Glycosaminoglycans | 20.9 (+/−1.7) | 53.2 (+/−3.1)* |

Results are presented as mean values (+/−95% CI)
*indicates significant difference (student's t-test, p < 0.05)

Example 3

Tissue strips were dissected from the wall of fresh (within 24 h of slaughter) and decellularised bladders using a scalpel and subjected to low strain-rate uniaxial tensile loading to failure. In order to study potential regional differences in the biomechanics of the bladder wall, five anatomical regions were tested, including the dorsal, ventral, lateral, trigone and lower body regions of the wall (FIG. 1). In each region, the anisotropy of the bladder wall was investigated by testing specimens along the apex-to-base and transverse directions. For each case, tissue strips measuring 20×5 mm were dissected and mounted onto a purpose built titanium holder (Korossis et al J Heart Valve Dis 11, 463, 2002). The holder was supported by a removable aluminium bracket that allowed alignment of the two holder parts, defined the gauge length of the specimens and ensured that no load was imposed on the specimen until the start of the test. The gauge length of the specimens was defined by a 10 mm wide central block separating the two holder parts and screwed onto the bracket. Prior to clamping, the thickness of the specimens was measured at 6 points along the long axis using a Mitutoyo thickness gauge (Mitutoyo, Andover, UK) with a resolution of 0.01 mm and the average thickness was recorded. During clamping, care was taken to mount the specimens under zero strain. Specifically, the specimen was floated onto the smooth clamp surface with minimum handling and secured in its completely relaxed state. Once the specimen was clamped onto the holder, the holder with the supporting bracket was secured to a Howden tensile machine and the bracket was removed. Testing was conducted in physiological saline at 20° C.

Prior to loading to failure, the specimens were preconditioned by cyclic loading using a double-ramp wave function until a repeatable load-elongation response was observed. For all specimens tested, a preconditioning period of 50 cycles was sufficient to produce a steady-state response. Following preconditioning, the specimens were loaded to failure using a positive ramp function at a rate of 10 mm/min. In order to obtain an accurate measure of the tissue gauge length, the tensile machine was set to produce a specimen preloading of 0.02 N, before the operating program started to acquire any data. Therefore, zero extension was taken at the point where a 0.02 N load was detected. The final gauge length of the specimen was calculated as the initial gauge length (10 mm) plus the extension that was needed to produce the specified preloading. Failure was taken to occur when the first decrease in load was detected during extension. The mode of failure observed was middle section necking and rupture for 90% of the specimens, independent of the specimen preparation, while the rest failed at the clamping point. During testing, load data from the load cell and extension data from the stroke of the tensile machine was acquired at a rate of 20 Hz. From the recorded load data the engineering stress ($\sigma$) was calculated as:

$$\sigma = \frac{F}{A_o}$$

where F is the acquired force in Newtons and $A_o$ the original cross-sectional area (CSA) of the undeformed specimen in mm². The CSA was calculated as $A_o$=w×t, where w is the width of the tissue strip (5 mm) and t its average thickness. The changes in thickness and width during preloading were considered negligible and were not taken into account. The engineering strain ($\epsilon$) was calculated from the extension data according to the formula:

$$\varepsilon = \frac{\Delta l}{l_o} \times 100$$

where $\Delta l$ is the extension of the specimen and $l_o$ its final gauge length.

The calculated stress-strain curves obtained for the specimens of each group were averaged over the number of specimens in each group (n=6) using a mathematical analysis software package (Origin v6.0, Microbal). The stress-strain behavior for each specimen was analyzed by means of six parameters. These have been described elsewhere (Korossis et al J Heart Dis 11, 463, 2002) and included the elastin (El-E) and collagen (Col-E) phase slopes, transition stress ($\sigma_{trans}$) and strain ($\epsilon_{trans}$), ultimate tensile strength (UTS) and failure strain ($\epsilon_{UTS}$). The biomechanical parameters of the specimens in each test group were averaged, and compared by student t-test.

Example 4

Whole porcine bladders were obtained from a local abattoir within 4 h of slaughter and transported to the laboratory on ice in sterile transport medium. The bladder stromal tissue was stripped of urothelium (Southgate et al Lab Invest, 71, 583, 1994) and smooth muscle cells isolated as previously described for human smooth muscle cells (Kimuli et al BJU Int 94, 859, 2004) were cultured in Dulbecco's Modified Eagle's Medium (DMEM) (Gibco, Paisley, UK) supplemented with 10% (v/v) fetal bovine serum (FBS) (Harlan, Loughborough, UK) and 1% (v/v) L-Glutamine (Sigma, Poole, UK) at 37° C. in a humidified atmosphere of 10% $CO_2$ in air. Morphological examination and immunohistological staining for smooth muscle actin (1A4) (Sigma, Poole, UK) was used to confirm cell strain identity and homogeneity of the cultures. Porcine smooth muscle (PSM) cell cultures were subcultured at confluence and maintained as finite cell lines through at least 15 passages.

Example 5

Decellularised bladder tissue was attached to the centre of a well in a 6-well culture plate using sterile adhesive Steri-strips (3M, Manchester, UK). Porcine smooth muscle cells (SM) (passage 2 to 7) were seeded into each well at a density of $1 \times 10^4$ cells/ml. As negative controls, SM cells were seeded into wells containing steri-strips without matrix and into wells without steri-strips or matrix. Plates were incubated at 37° C., 10% $CO_2$ for 48 h, 4 days or 12 days. Medium was then removed from each well, and the wells washed with PBS and stained/fixed with 1% (w/v) crystal violet (Sigma, Poole, UK) in 20% (v/v) ethanol before visualization by light microscopy.

Example 6

SM cells were suspended in growth medium at $1 \times 10^4$ cells/ml and 200 µL was added to the individual wells of a 96-well plate. Cells were left to attach at 37° C., 10% $CO_2$ for 2 h. A 5 $cm^2$ sheet of decellularised bladder matrix was diced and added to 50 ml DMEM. After 24 h on a shaker the medium was removed, filter-sterilised through a 0.2-µm filter and supplemented with 0%, 5% or 10% (v/v) FBS. As a control, non-conditioned medium was prepared in a similar way, except for omitting the diced bladder matrix. The appropriate conditioned or non-conditioned medium was used to replace the medium on the cells in the 96-well plate in replicates of six and the plates were incubated at 37° C. in a humidified atmosphere of 10% $CO_2$ in air. 3-[4,5-dimethyl (thiazol-2-yl)-3,5-diphery]tetrazolium bromide [(MTT) Sigma, Poole, UK] assays were used to compare the viability of SM cells grown in control or decellularised matrix-conditioned media. A single plate was removed on days 0, 1, 4 and 7 to assess cell viability with the MTT assay. MTT (200 µL, 0.5 mg/ml) was added to each well on appropriate days and left to incubate for 4 h at 37° C. The MTT was replaced by 200 µL of DMSO and mixed well to dissolve formazan crystals. The absorbance was read at 570 nm using a plate reader.

Example 7

In order to determine whether SM cells were able to repopulate the decellularised tissue, suspensions of $2 \times 10^5$ SM cells (at passages 2-7) in 200 µl DMEM were added to decellularised tissue samples in 6-well plates and allowed to attach for 2 h after which time the wells were flooded with complete DMEM. As a control, 200 µl of cell-free DMEM was added to tissue samples in wells that were flooded with complete DMEM as before. Seeded and non-seeded samples were collected on days 1, 3, 7, 14 and 21 in duplicate, washed in PBS and fixed in 10% formalin for histological assessment.

Example 8

Figure 2:
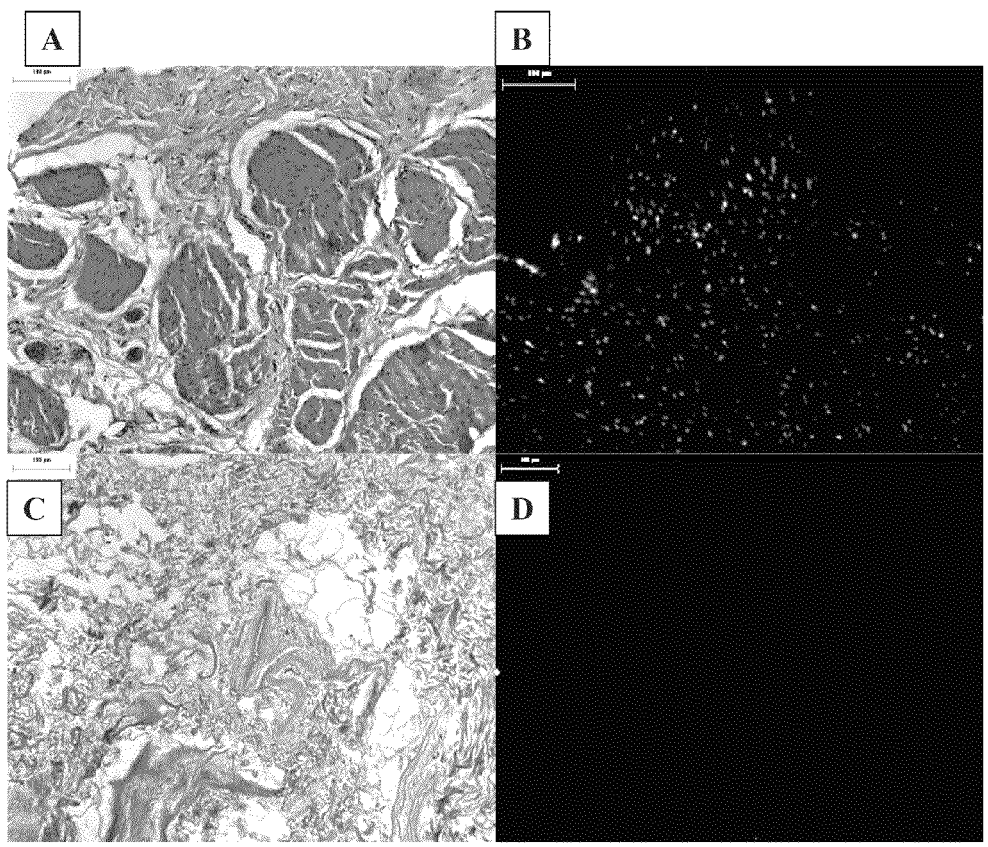
FIG. 2 shows histological characterisation of fresh (A, B) and decellularised (C, D) porcine bladder. Sections were stained with haematoxylin and eosin (A and C) and Hoeschst 33258 (B and D). Scale bar—100 µm.
Figure 3:
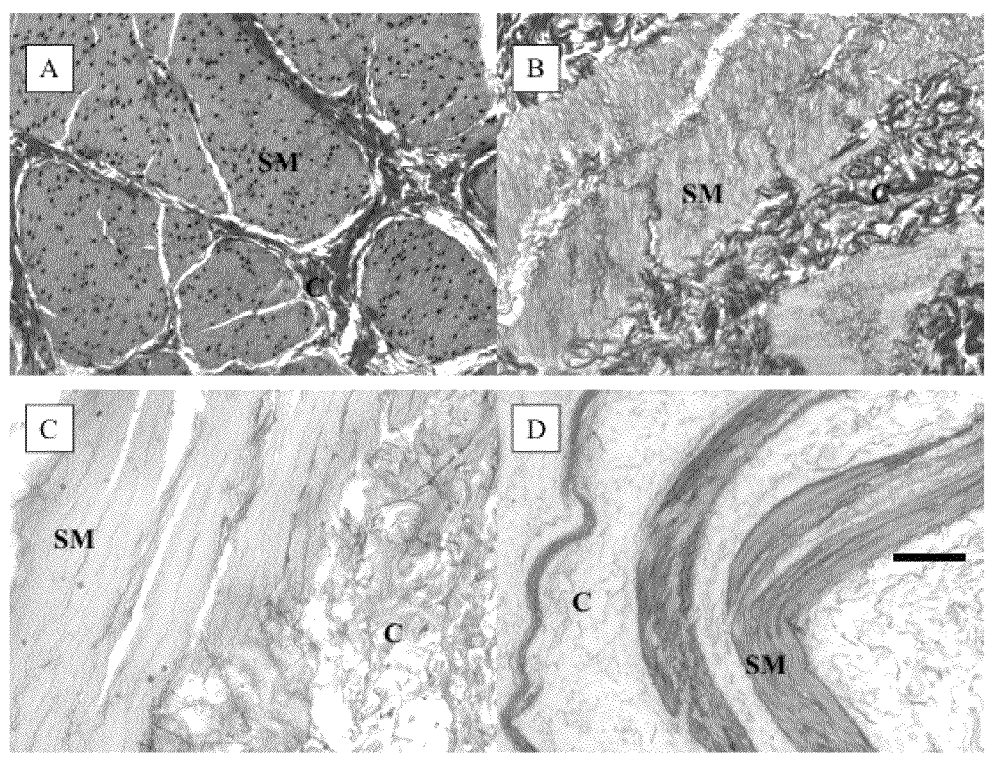
FIG. 3 shows histological characterisation of fresh (A and C) and decellularised (B and D) porcine bladder. Paraffin-wax-embedded sections were stained with Van Gieson (A and B) and Miller's Elastin stain (C and D) [SM: Smooth Muscle, C: Collagen matrix]. Scale bar—100 µm.
Figure 4:
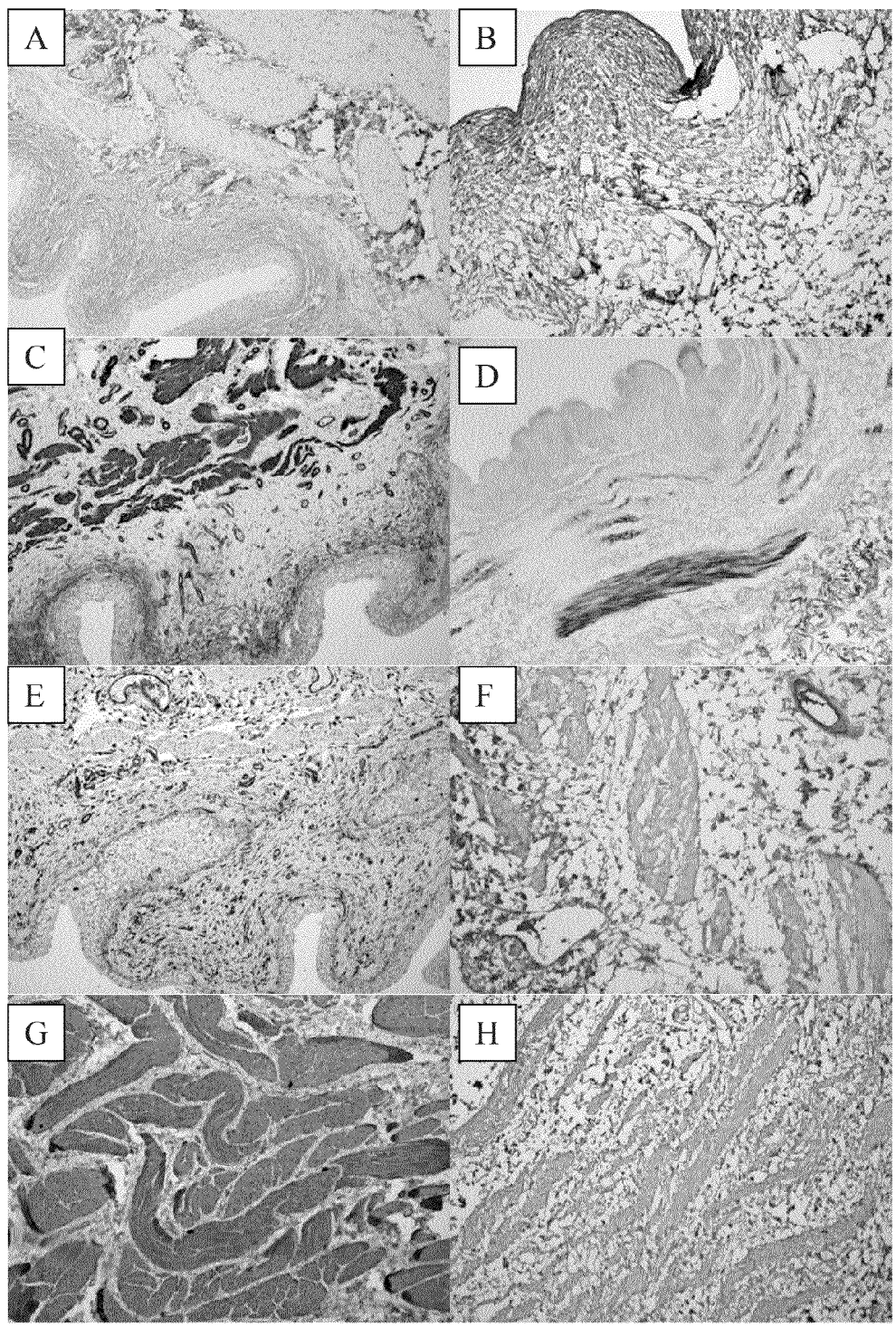
FIG. 4 shows immunoperoxidase labelling of fresh (A, C, E and G) and decellularised (B, D, F and H) porcine bladder. Sections labelled with antibodies against collagen type I (A and B), smooth muscle actin (C and D), vimentin (E and F) and desmin (G and H) were counterstained with haematoxylin and show a qualitative reduction in smooth muscle actin and desmin.
Figure 5:
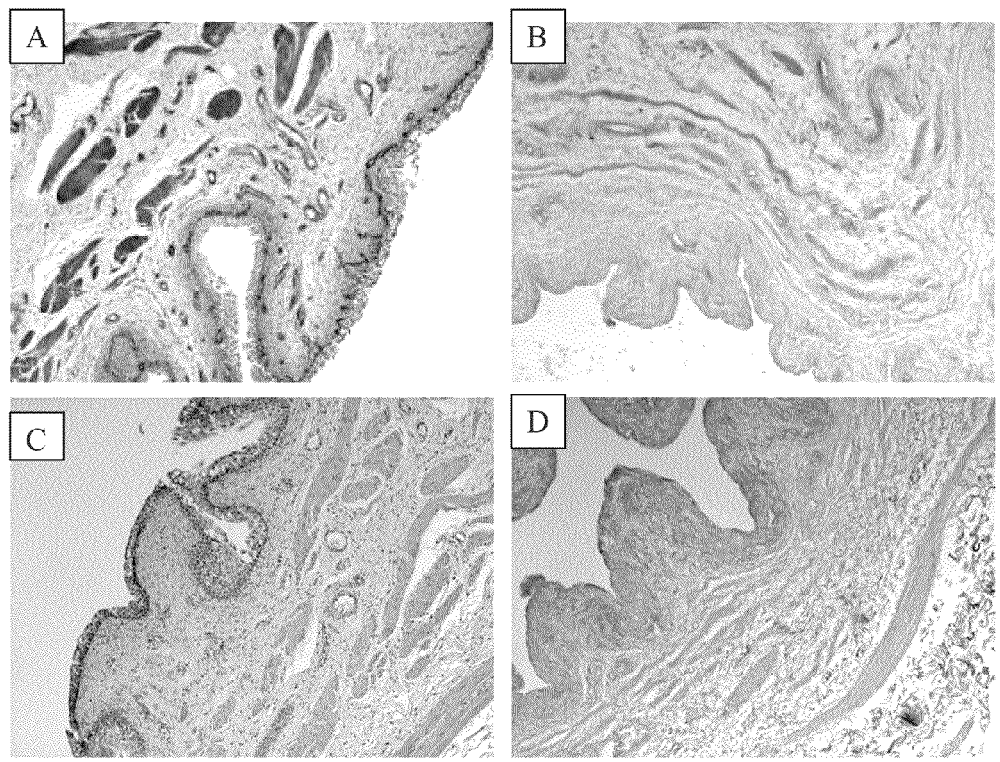
FIG. 5 shows immunoperoxidase labelling of fresh (A and C) and decellularised (B and D) porcine bladder. Sections labelled with antibodies against collagen type IV (A and B) and laminin (C and D) were counterstained with haematoxylin.

The complete decellularisation of porcine bladder was confirmed histologically. Compared to native bladder, matrices were completely devoid of urothelium and there were no cells present within the underlying tissue. This was confirmed by Hoechst 33258 staining of sections to visualize cell nuclei (FIG. 2). Both Miller's elastin stain and the Van Gieson technique showed the general structure of the decellularised matrix to resemble that of native bladder (FIG. 3). Immunolabelling with antibodies to αSMA, desmin and vimentin indicated that some poorly soluble cytoskeletal components of smooth muscle were not removed by the decellularisation process (FIG. 4). Negative staining for collagen type IV and laminin, however, confirmed removal of the basement membrane from the bladder lumen (FIG. 5).

Example 9

Figure 6:
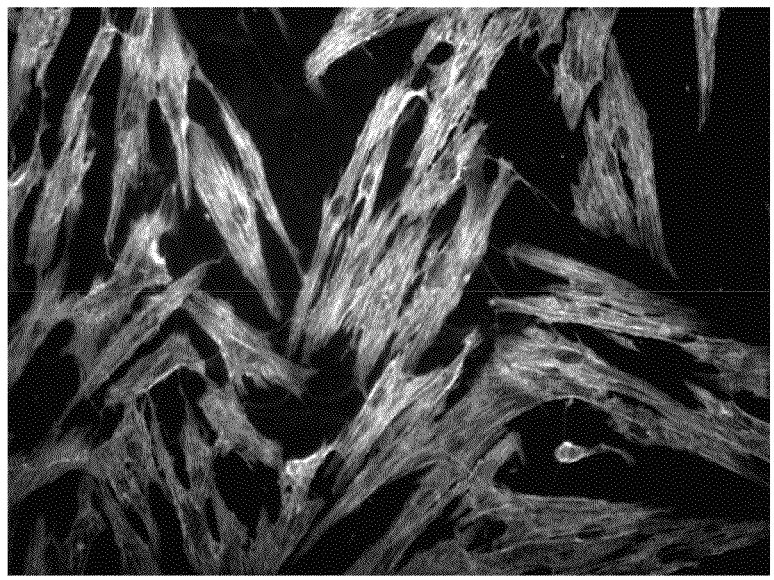
FIG. 6 shows immunofluorescence labelling of SM cells labelled with an antibody to smooth muscle actin (A). Hoescht 33258 dye was used to identify all nuclei in an equivalent field of view (B). Scale bar 50 µm.
Figure 6:
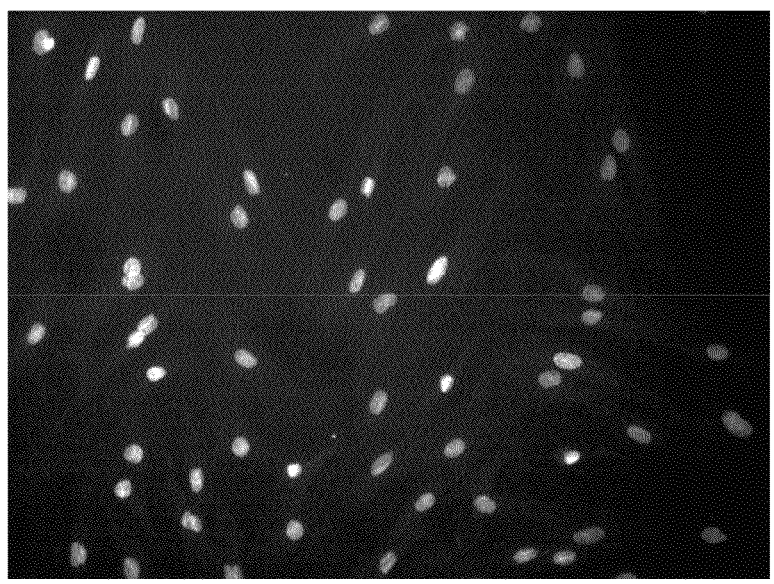
Figure 7:
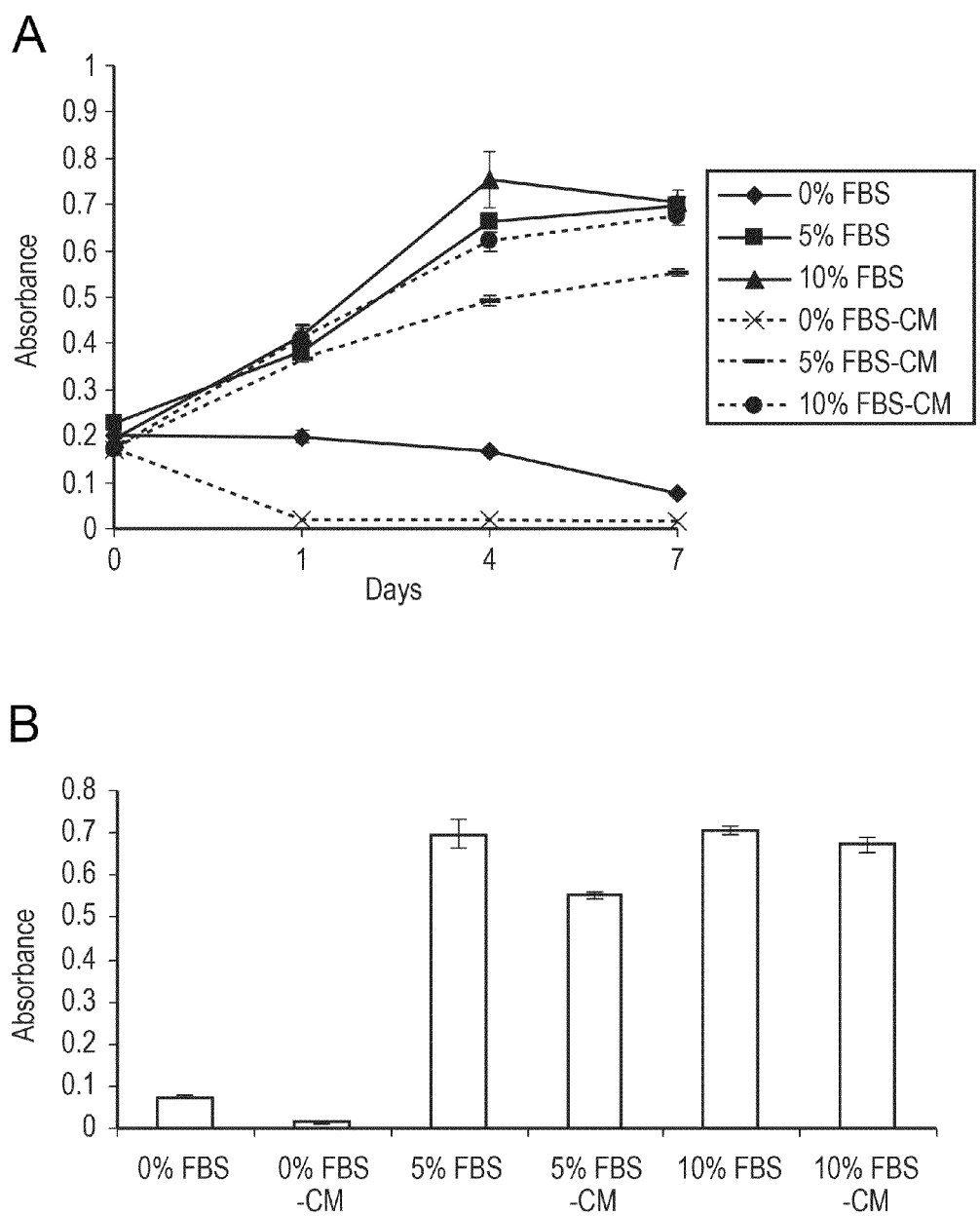
FIG. 7 (A) shows SM cell proliferation assessed by MTT assay over 7 days and FIG. 7 (B) on day 7. The graphs show that in the presence of 10% (v/v) serum, proliferation of SM cells was not inhibited by medium preconditioned by incubation with the decellularised matrix. Absorbance was measured in replicates of six and the calculated SEM plotted as x and y error bars.

MTT assay showed that porcine cells, smooth muscle in origin (FIG. 6), underwent growth in a concentration-dependent manner as the percentage of serum in the medium increased from 0 to 10% (v/v) (FIG. 7). Smooth muscle cells cultured in DMEM conditioned with the decellularised matrix showed a similar concentration-dependent growth. There was no statistical difference between the ultimate biomass of cells grown in control or conditioned medium under standard culture conditions.

Figure 8:
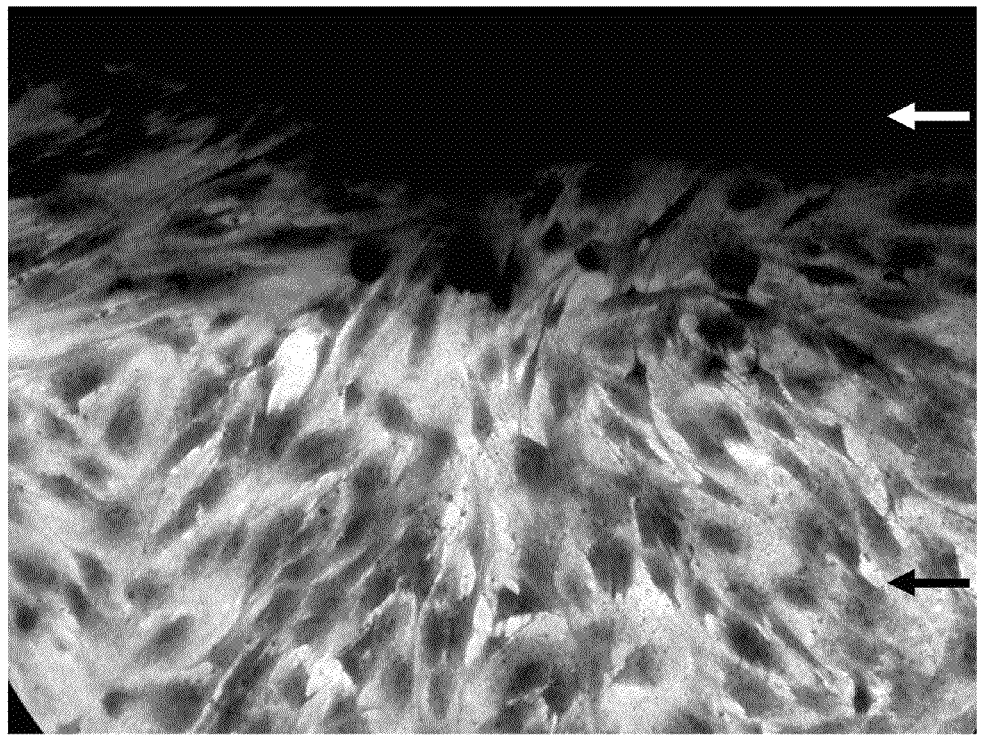
FIG. 8 shows a phase-contrast micrograph showing porcine SM cells growing up to the decellularised matrix (DM) indicating that the matrix was not cytotoxic. Scale bar 50 µm.
Figure 9:
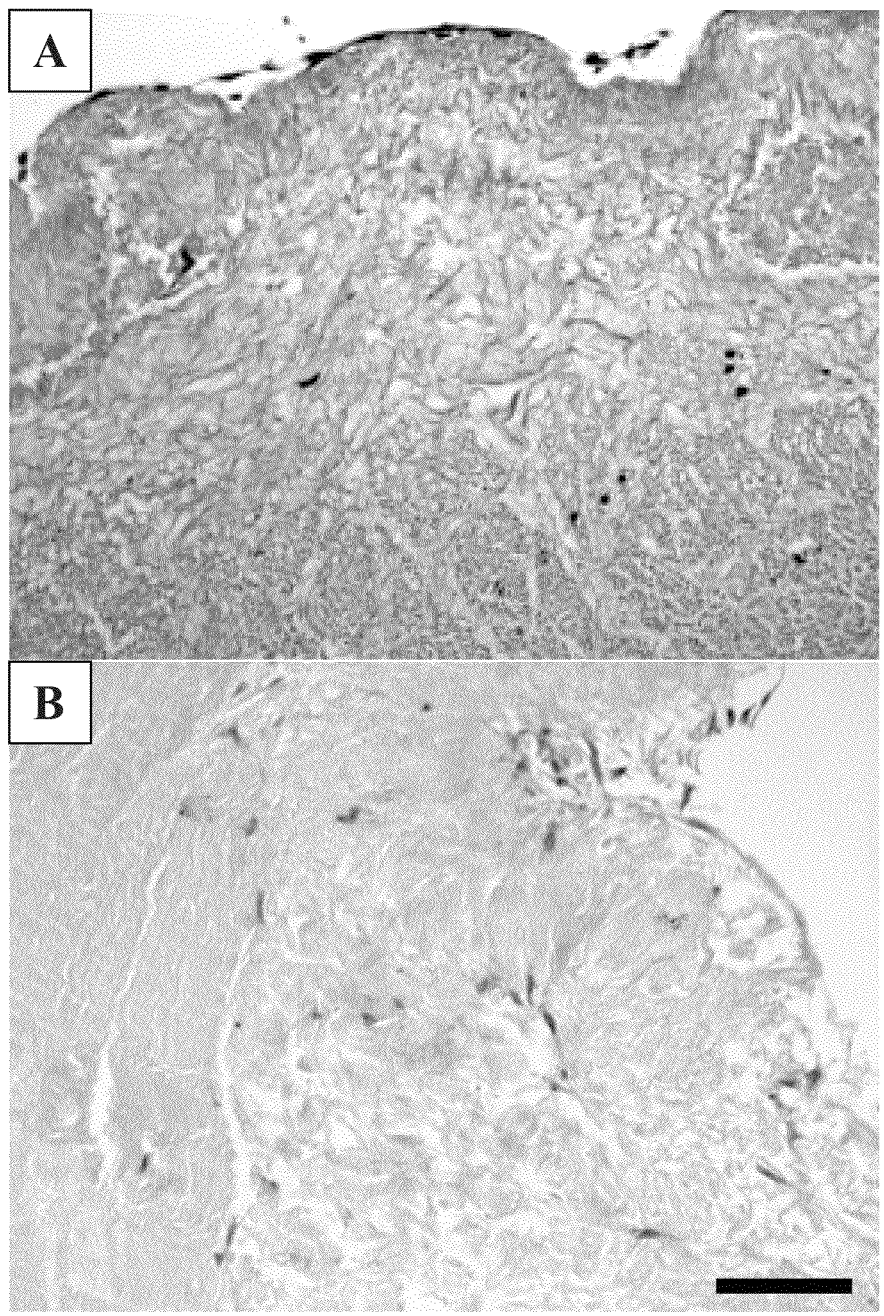
FIG. 9 shows an H&E stained section showing porcine SM cells seeded onto the decellularised porcine bladder matrix. (A) After 14 days in culture, there is a single layer of cells lining the surface of the matrix and some cells are seen to have infiltrated. (B) Further matrix penetration has occurred after 21 days. The matrix showed no signs of degradation, Scale bar 100 µm.

Smooth muscle cells grew up to the decellularised matrix with no evidence of contact inhibition (FIG. 8) providing evidence that the decellularised matrix was not cytotoxic. Smooth muscle cells were able to attach and form a confluent monolayer of cells across the surface of the decellularised matrix after 3 days in culture. Under static culture conditions, there was no cell penetration into the matrix after 7 days. After 14 days, however, cells had begun to infiltrate the matrix and by 21 days had infiltrated to a depth approximately $\frac{1}{3}^{rd}$ that of the matrix (FIG. 9).

Example 10

The amount of DNA per mg dry weight of porcine bladder tissue before and after decellularisation was 2.8 (+/−0.1) $\mu g \cdot mg^{-1}$ and 0.1 (+/−0.1) $\mu g \cdot mg^{-1}$, respectively (Table 1—see under Example 1). There was a significant decrease in the DNA content of tissue after decellularisation (t-test; p<0.001). The concentrations of hydroxyproline and GAGs per mg dry weight of porcine bladder tissue before and after decellularisation were also significantly different, with the relative proportion of each being significantly higher in the decellularised tissue (t-test; p<0.001) reflecting the differential removal of other components.

Example 11

Figure 10:
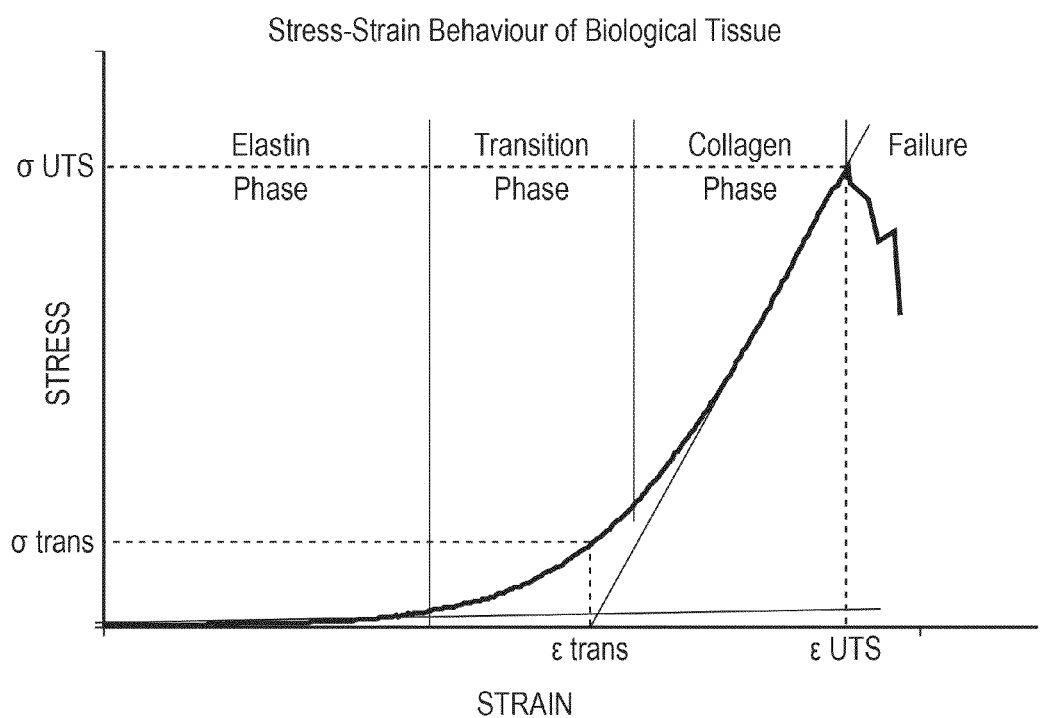
FIG. 10 shows the phases of biological tissue stress-strain behaviour.

Tissue strips dissected from the wall of fresh and decellularised bladders were subjected to low strain-rate uniaxial tensile loading to failure. The stress-strain behaviour is shown in FIG. 10. In order to study potential regional differences in the biomechanics of the bladder wall, five anatomical regions were tested, including the dorsal, ventral, lateral, trigone and lower body regions of the wall. In each region, the anisotropy of the bladder wall was investigated by testing specimens along the apex-to-base and transverse directions. Table 2 shows the results of biomechanical tests, thickness, elastin and collagen phase slope, transition stress and strain, ultimate tensile strength and failure strain.

TABLE 2

Uniaxial tensile strength testing of fresh and decellularised porcine bladder tissue.

| Bio-mechanical test results (Mean values) | Fresh bladder tissue Apex to Base (top row) Transverse (bottom row) | | | | | Decellularised bladder tissue Apex to Base (top row) Transverse (bottom row) | | | | |
|---|---|---|---|---|---|---|---|---|---|---|
| | Dorsal | Ventral | Lower Body | Trigone | Lateral | Dorsal | Ventral | Lower Body | Trigone | Lateral |
| Thickness (mm) | 1.311 | 1.285 | 1.790 | 1.491 | 1.264 | 0.594 | 0.696 | 0.647 | 0.829 | 0.604 |
| | 1.299 | 1.222 | 1.577 | 1.309 | 1.425 | 0.552 | 0.614 | 0.589 | 0.836 | 0.729 |
| Elastin phase slope [GPa $(\times 10^{-5})$] | 2.87 | 3.39 | 2.18 | 3.21 | 3.81 | 37.8 | 6.09 | 16.0 | 10.3 | 21.9 |
| | 3.78 | 1.91 | 1.85 | 3.34 | 3.87 | 33.4 | 15.2 | 9.48 | 10.1 | 10.8 |
| Collagen phase slope [GPa $(\times 10^{-4})$] | 9.41 | 6.51 | 21.4 | 20.6 | 15.2 | 44.2 | 36.4 | 37.2 | 49.2 | 78.5 |
| | 5.43 | 5.64 | 6.17 | 8.83 | 6.12 | 33.1 | 44.1 | 24.1 | 14.0 | 17.2 |
| Transition stress (MPa) | 0.148 | 0.184 | 0.302 | 0.183 | 0.288 | 0.282 | 0.275 | 0.270 | 0.522 | 0.496 |
| | 0.110 | 0.166 | 0.141 | 0.151 | 0.192 | 0.156 | 0.322 | 0.197 | 0.164 | 0.175 |
| Transition strain (%) | 126.52 | 119.17 | 153.63 | 87.11 | 152.72 | 27.63 | 37.82 | 40.77 | 62.83 | 55.23 |
| | 117.05 | 172.30 | 171.40 | 128.55 | 166.84 | 25.41 | 32.65 | 47.42 | 51.90 | 33.21 |
| Ultimate tensile strength (MPa) | 1.036 | 0.943 | 1.541 | 1.091 | 1.562 | 1.995 | 1.250 | 2.018 | 2.254 | 3.058 |
| | 0.741 | 0.709 | 0.907 | 0.815 | 0.833 | 1.199 | 1.766 | 1.173 | 1.020 | 0.801 |
| Failure strain (%) | 266.63 | 314.73 | 237.20 | 158.65 | 281.92 | 84.30 | 86.59 | 100.03 | 120.96 | 115.93 |
| | 304.38 | 321.47 | 340.97 | 245.95 | 316.73 | 80.59 | 79.69 | 110.14 | 139.60 | 85.67 |

The results showed that decellularised bladder tissue samples are significantly thinner than the fresh bladder samples. In fresh bladder samples, the collagen phase slope values are higher in samples retrieved in an apex to base direction than in transverse samples. In addition, samples retrieved in an apex to base direction also have increased ultimate tensile strength compared to equivalent transverse samples and their failure strain is reduced.

As regards the collagen and elastin phase slope values of decellularised bladder tissue samples, these are increased compared to fresh bladder tissue samples. Collected in an apex to base direction, decellularised samples have increased ultimate tensile strength compared to equivalent fresh samples. No significant differences in the ultimate tensile strength of decellularised and fresh samples collected in a transverse direction were observed.

The results also showed that decellularised bladder samples have decreased failure strain values as compared to fresh bladder samples and that whilst transitional stress values do not differ significantly between fresh and decellularised bladder tissue samples, there is a decrease in the transitional strain values of decellularised samples.

Decreased strain values and increased collagen and elastin phase slopes indicate that the decellularised tissue is stiffer than fresh tissue (that the application of load results in less deformation per unit length of tissue).

Example 12

Figure 11:
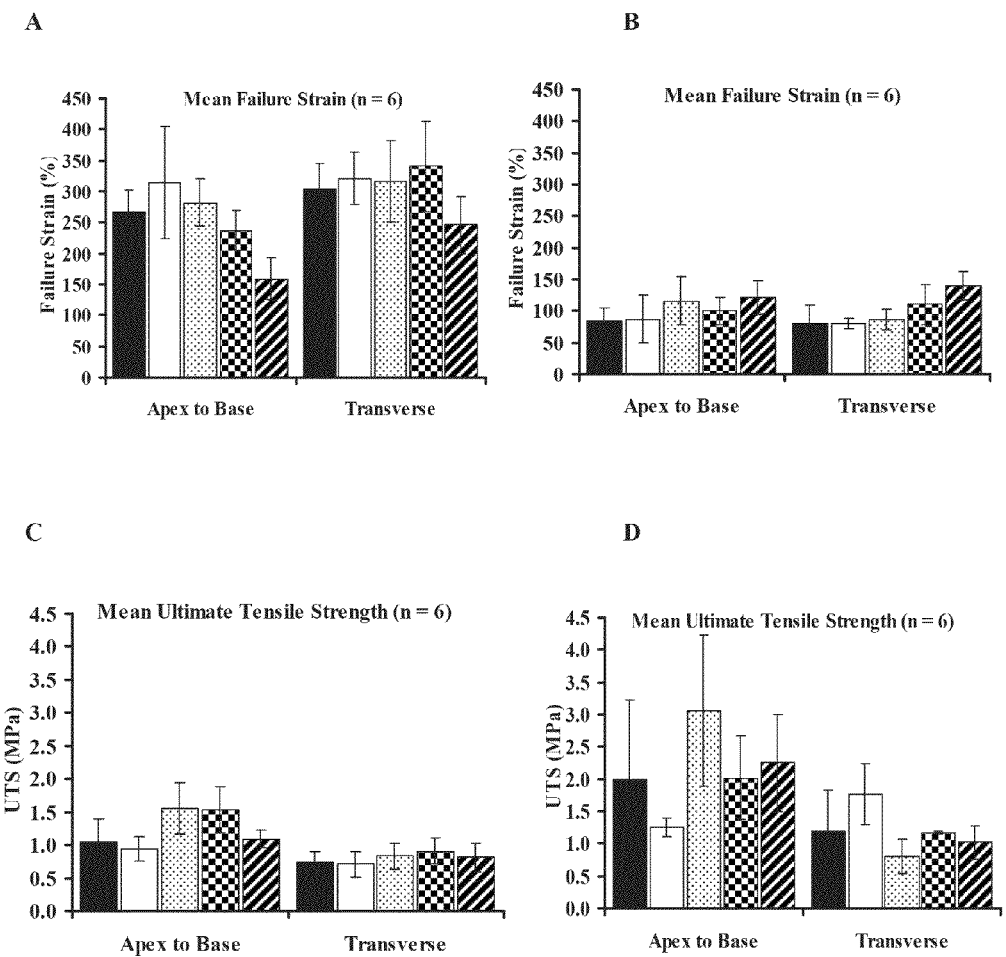
FIG. 11 shows biomechanical testing of fresh and decellularised porcine bladder tissue (n=6). Each test was performed in two directions: apex-to-base and transverse; and on samples from 5 different anatomical regions of the bladder. Results are presented as mean values (+/−95% CI).
Figure 11:
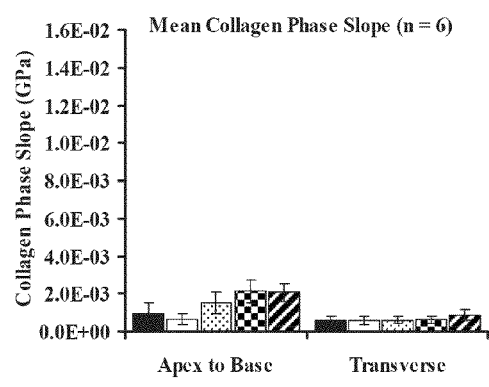
Figure 11:
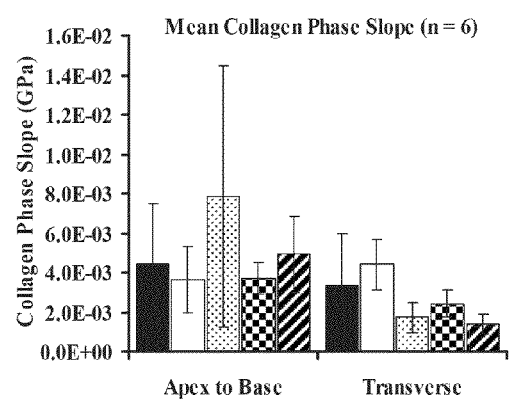

The biomechanical properties of fresh (FIGS. 11A, C and E) and decellularised (FIGS. 11B, D and E) bladder tissues were established by uniaxial tensile loading to failure of bladder wall strips from five anatomical regions of the bladder, namely the trigone, lower body, lateral, ventral and dorsal regions. Comparison of the results from the five anatomical bladder regions showed that different regions of the bladder demonstrated different mechanical behaviour as depicted by varying values for the collagen phase slope (FIGS. 11E and F), failure strain (FIGS. 11A and B) and ultimate tensile strength (FIGS. 11C and D). Moreover, significant anisotropy was also found between the apex-to-base and transverse directions.

Collagen phase slope and average failure strain values were significantly changed following decellularisation, representing decreased extensibility (t-test, $p=<0.05$), However, the ultimate tensile strength (UTS) of the decellularised bladder wall was not significantly different from that of the fresh bladder wall (t-test, $p=>0.05$).

Example 13

Bladder wall specimens were subjected to suture retention testing. Tissue strips measuring 10×5 mm were dissected from the lateral region of the wall of fresh and decellularised bladders, along the apex-to-base direction, and mounted onto the titanium holder, described above. The specimens were mounted so that only one end of the specimen was clamped to the holder. One polypropylene suture (4-0, Ethicon) with 2 mm bite depth was attached to the other end of the specimen. The suture was then secured to the upper part of the holder. Subsequently, the holder with the supporting bracket was secured to the Howden tensile machine and the bracket was removed. The suture was then pulled under uniaxial loading at a rate of 10 mm/min, and the suture pull-out force was recorded.

Figure 12:
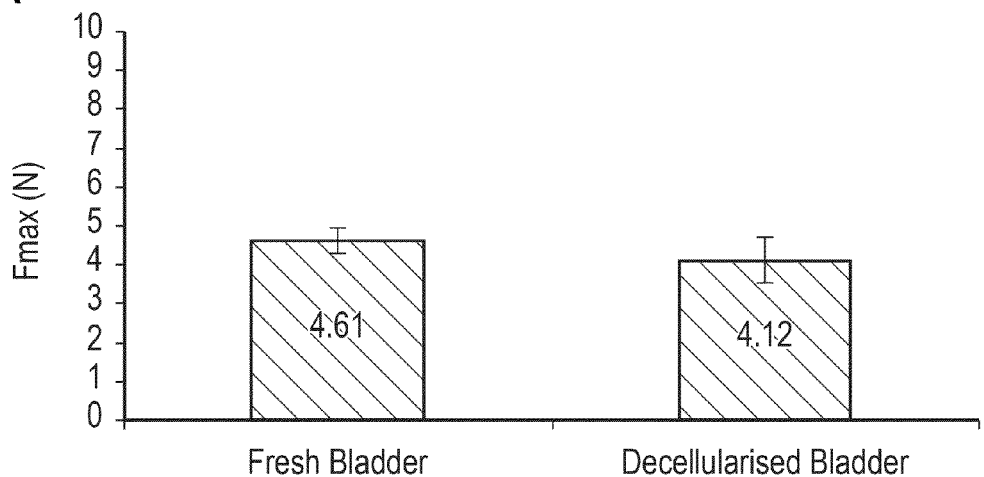
FIG. 12 shows determination of the (A) suture retention strength and (B) burst pressure of fresh and decellularised porcine bladder tissue. Suture retention tests were performed on bladder strips and burst pressure tests on intact bladder specimens. In each case, n=6 and the results are presented as mean values (+/−95% CI).
Figure 12:
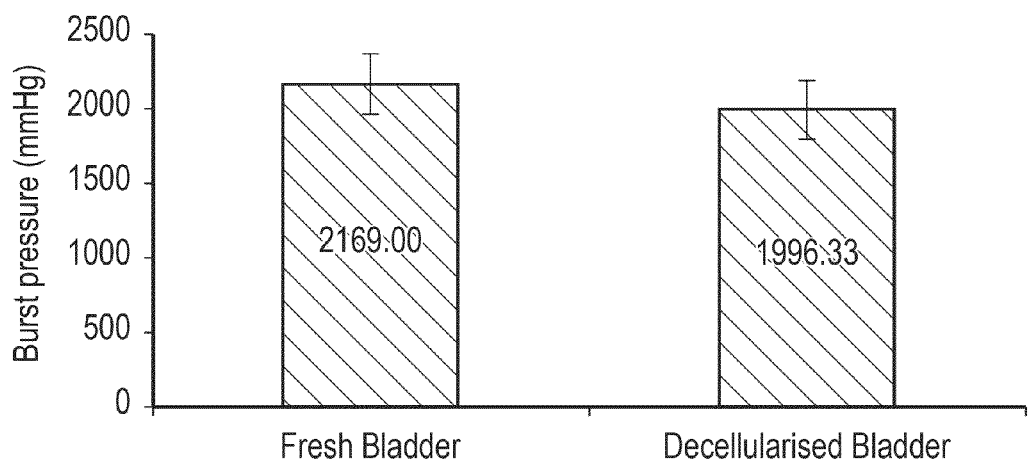

There was no significant difference in the ability of fresh and decellularised bladder tissue to retain sutures under force (t-test, $p>0.05$); nor in the amount of pressure required to burst intact fresh or decellularised bladders (t-test, $p>0.05$, FIG. 12).

Figure 13:
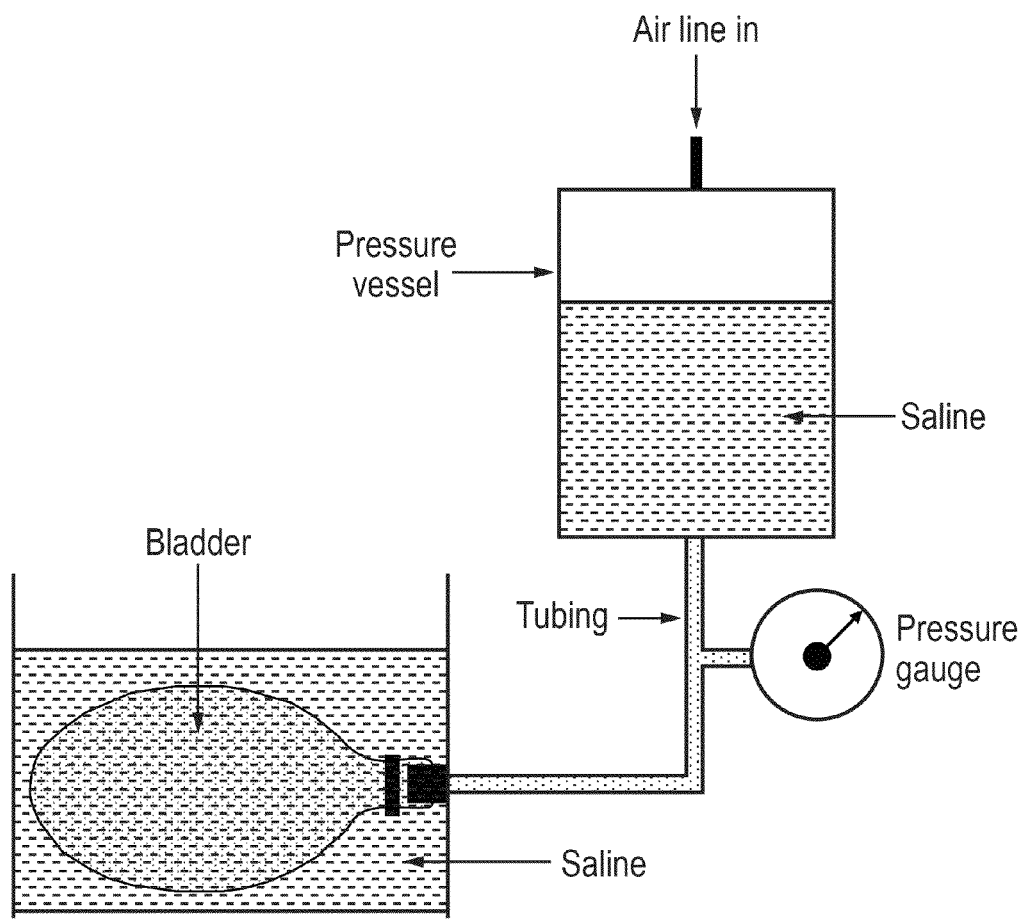
FIG. 13 shows a burst pressure rig for testing of fresh and decellularised bladder burst testing.

Fresh and decellularised whole bladders were subjected to burst testing. For this purpose a burst pressure rig was developed (FIG. 13). The rig comprised of a pressure vessel, which generated the test pressures, a pressure gauge for measuring the applied hydrostatic pressures, and a container filled with saline, which accommodated the bladder under testing. Pressurised air, supplied at a rate of 20 ml/s, was used to pressurise the vessel, which was ¾s filled with saline. The inflow of air in the vessel caused the pressurisation of the saline and the subsequent filling and inflation of the bladder, which was connected via silicone tubing to the pressure vessel. The pressure of the saline was increased until bursting of the bladder was achieved, and the maximum pressure just before bursting was recorded. There was no significant difference in the burst pressure of fresh and decellularised porcine bladder tissue (FIG. 12).

Example 14

The biomechanical properties of fresh and decellularised bladder tissues were compared with other membranous tissues that might be used in the repair of the bladder. These included fresh porcine pericardium, decellularised porcine pericardium, SIS™ and Permacol™ (FIGS. 14-21).

Figure 14:
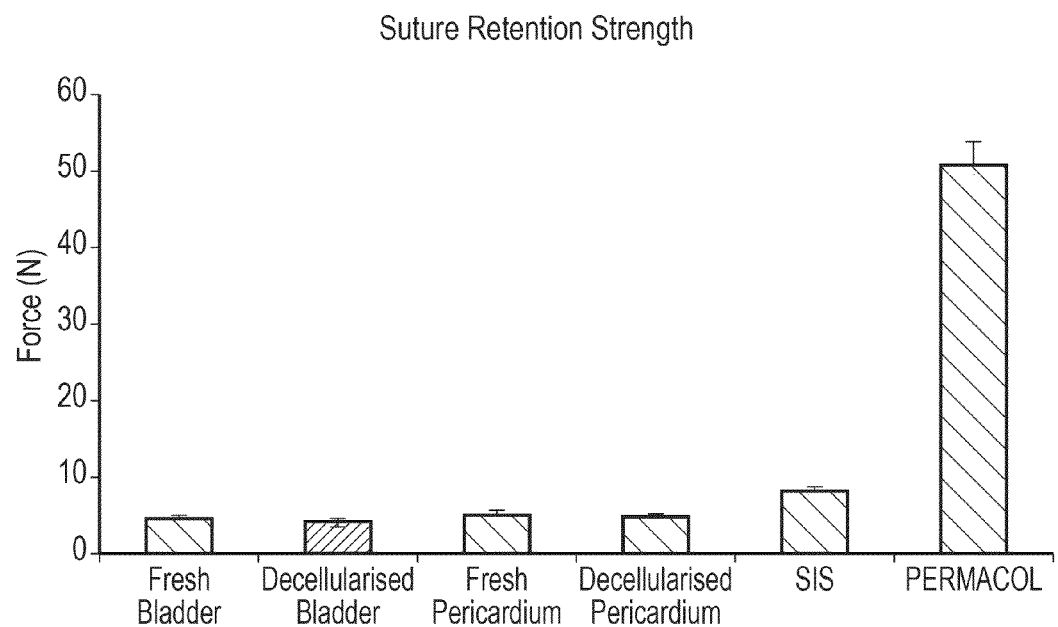
FIG. 14 is a bar chart comparison representation of suture retention strength between fresh bladder, decellularised bladder, fresh pericardium, decellularised pericardium and SIS™ and PERMACOL™ implants respectively.
Figure 15:
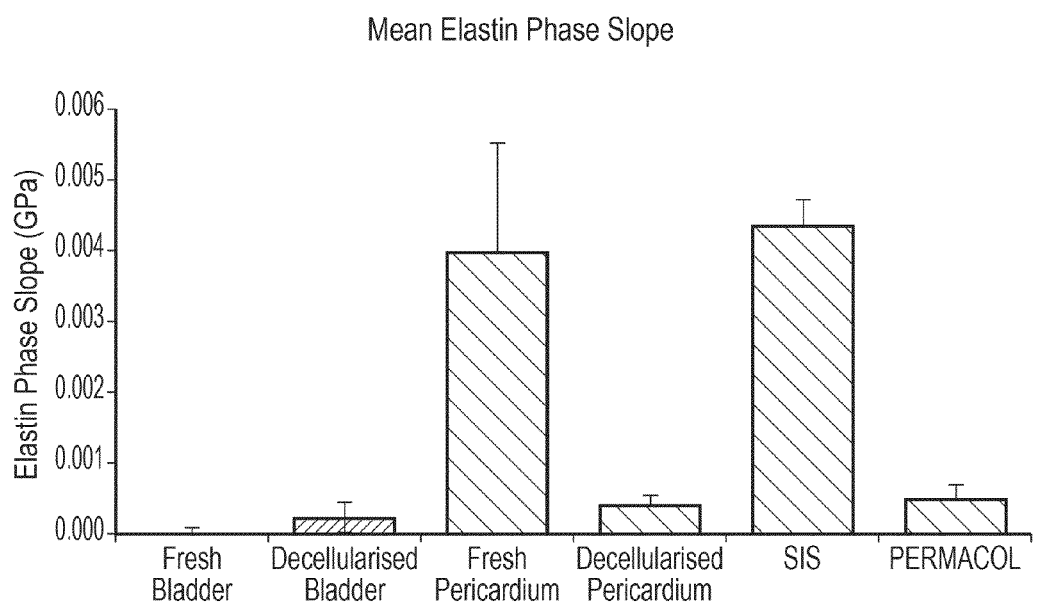
FIG. 15 is a bar chart comparison representation of mean elastin phase slope between fresh bladder, decellularised bladder, fresh pericardium, decellularised pericardium and SIS™ and PERMACOL™ implants respectively.
Figure 16:
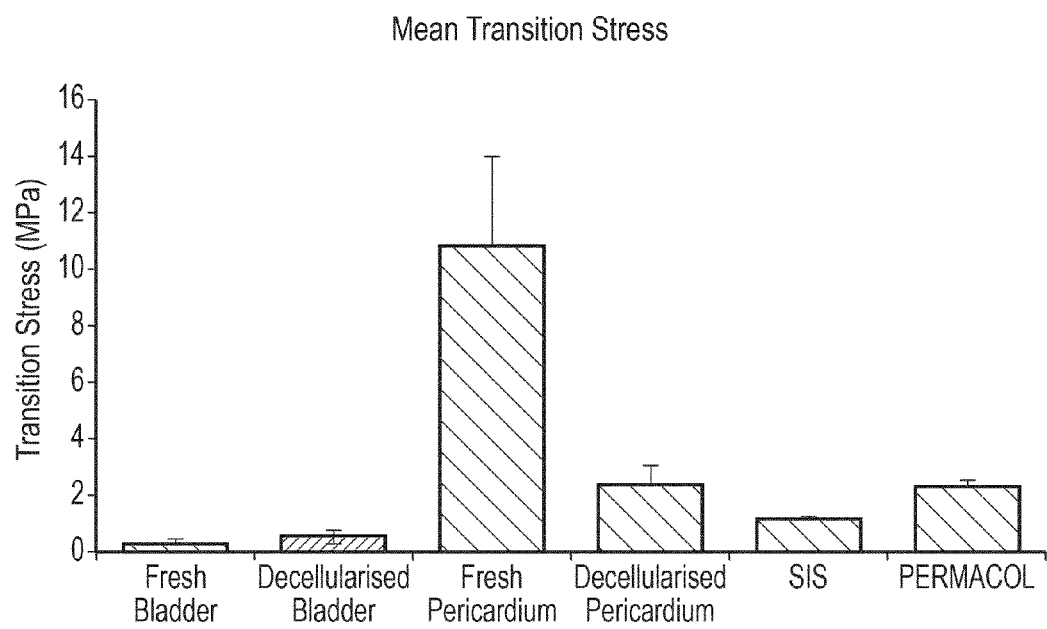
FIG. 16 is a bar chart comparison representation of mean transition stress between fresh bladder, decellularised bladder, fresh pericardium, decellularised pericardium and SIS™ and PERMACOL™ implants respectively.
Figure 17:
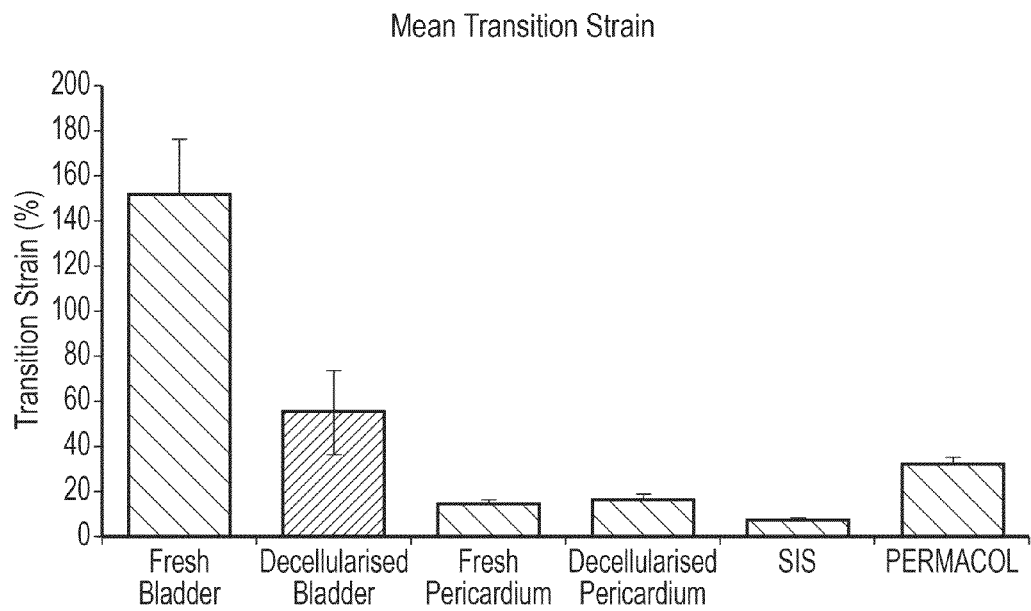
FIG. 17 is a bar chart comparison representation of mean transition strain between fresh bladder, decellularised bladder, fresh pericardium, decellularised pericardium and SIS™ and PERMACOL™ implants respectively.
Figure 18:
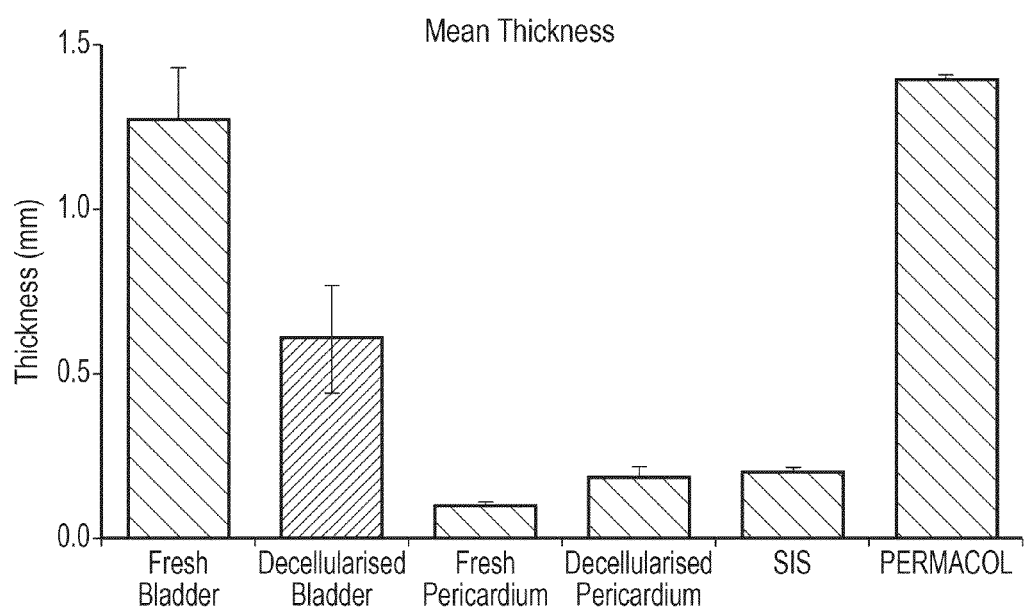
FIG. 18 is a bar chart comparison representation of mean thickness between fresh bladder, decellularised bladder, fresh pericardium, decellularised pericardium and SIS™ and PERMACOL™ implants respectively.
Figure 19:
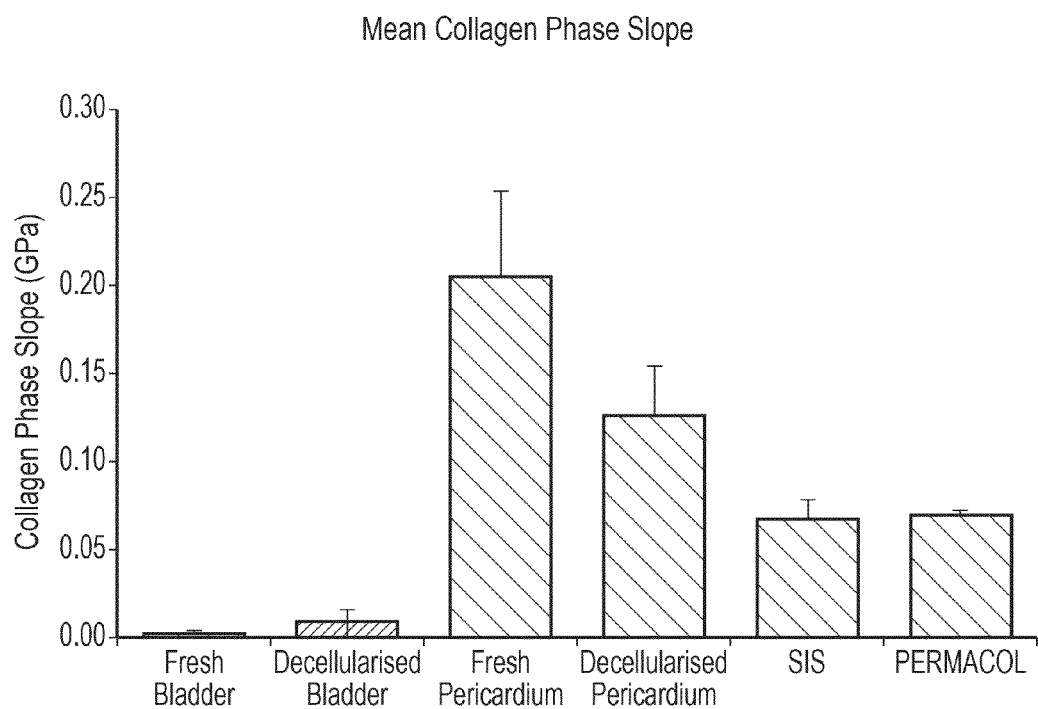
FIG. 19 is a bar chart comparison representation of mean collagen slope between fresh bladder, decellularised bladder, fresh pericardium, decellularised pericardium and SIS™ and PERMACOL™ implants respectively.
Figure 20:
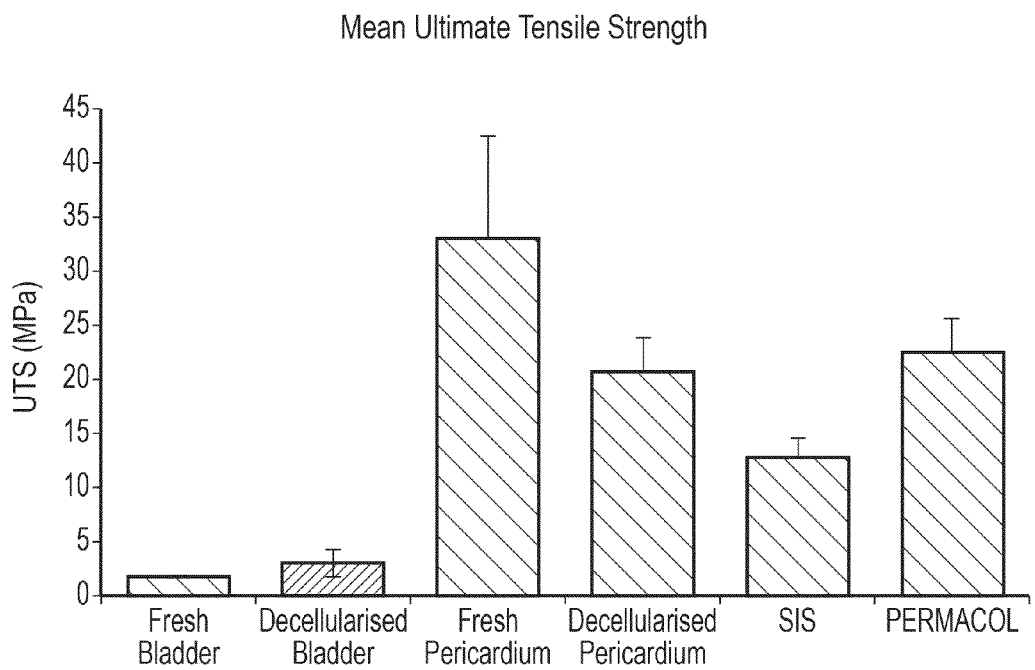
FIG. 20 is a bar chart comparison representation of mean ultimate tensile strength between fresh bladder, decellularised bladder, fresh pericardium, decellularised pericardium and SIS™ and PERMACOL™ implants respectively.
Figure 21:
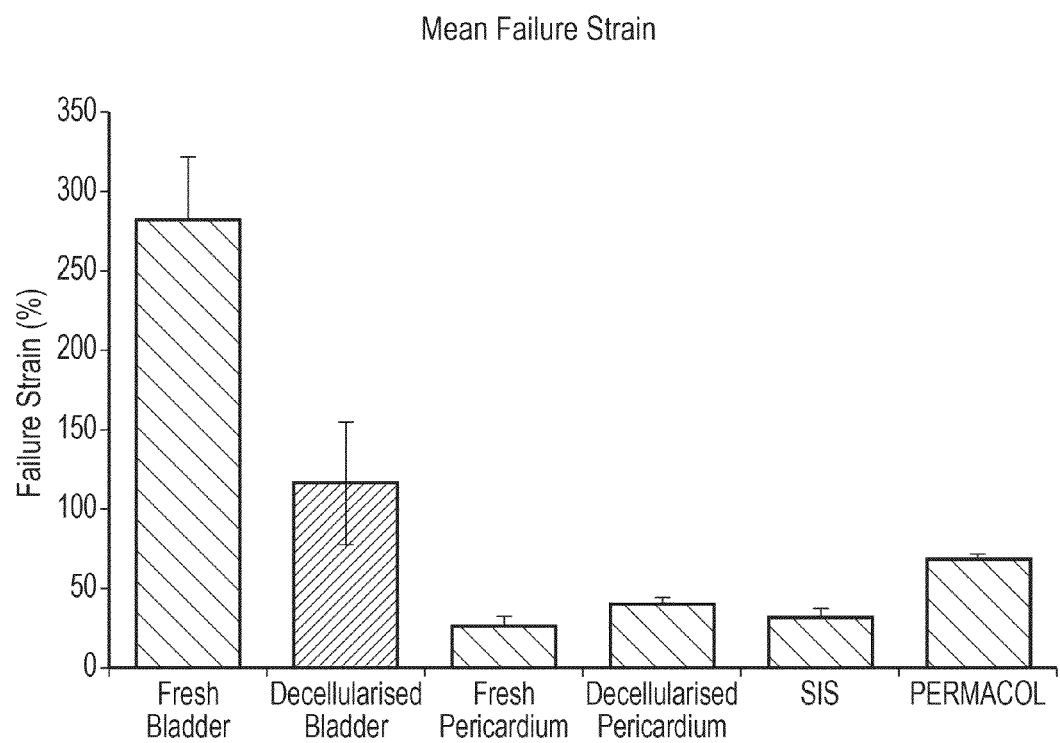
FIG. 21 is a bar chart comparison representation of mean failure strength between fresh bladder, decellularised bladder, fresh pericardium, decellularised pericardium and SIS™ and PERMACOL™ implants respectively.

The decellularised porcine bladder, fresh and decellularised porcine pericardia all showed similar suture retention strength which was significantly lower (p<0.05; ANOVA) than that of SIS™ and Permacol™ (FIG. 14). The mean elastin phase slope, collagen phase slope, transition stress and ultimate tensile strength of the decellularised bladder material were not significantly different to those properties of the fresh bladder (p<0.05; ANOVA) compared to other biomaterials. These comparisons indicate that decellularised bladder matrix would make the most suitable replacement for bladder tissue with regard to biomechanical properties.

Example 15

In order to determine the in vivo biocompatibility of the acellular porcine bladder biomaterial, the reaction to the material was compared to that of fresh porcine bladder tissue in a mouse subcutaneous implant model.

Following a short term general anaesthesia, two 5 mm² pieces of fresh or acellular porcine bladder were implanted subcutaneously in normal mice (female 6-8 week old mf-1 hairless mice; n=3 in each group). Mice were sacrificed at three months and the implants and the overlying skin were retrieved. The explanted tissues were cryoembedded in OCT and sections (5 □m) cut in a cryostat. Representative sections from throughout the tissue were stained with haematoxylin and eosin to visualize the general histioarchitecture. The cellular infiltrate in the tissues was determined by immunoperoxidase staining using rat monoclonal antibodies to mouse CD3 (pan T-cells; IgG2a; Caltag) and F4/80 (macrophages; IgG2b; Caltag). Goat anti-rat IgG conjugated to biotin was used as the secondary antibody. Appropriate negative controls were included. Representative images were captured digitally.

Figure 22:
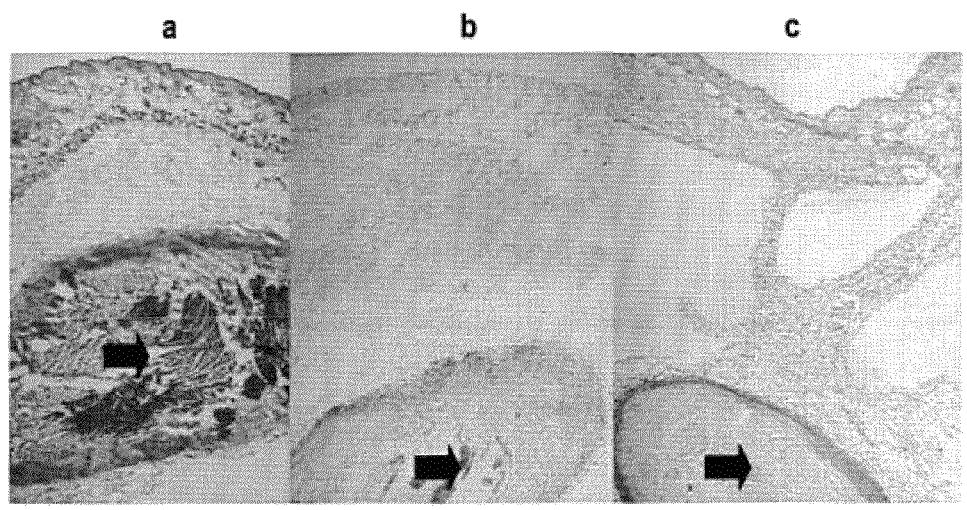
FIG. 22 shows explanted fresh bladder tissue stained with (a) haematoxylin and eosin (b) Anti-CD3 (pan T-cell) and (c) Anti f4/80 (macrophage). Magnification is at ×40 and arrows indicate implanted tissue.

The fresh tissue explants were encapsulated by cells which were predominantly F4/80 (macrophage) or C3 (T-cell) positive (FIG. 22). The tissues showed signs of vacuolation/disintegration and there were very few cells present within the matrix of the implanted fresh tissues. The pattern was indicative of a foreign body response to the implanted fresh tissues.

Figure 23:
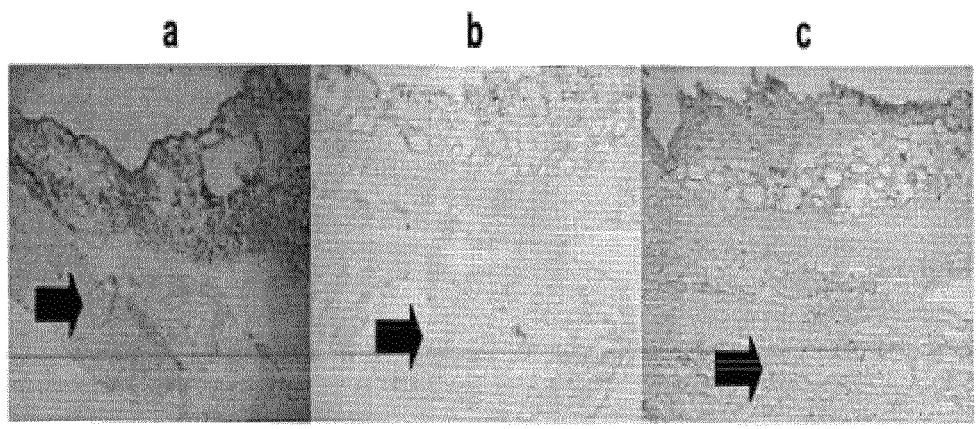
FIG. 23 shows explanted acellular bladder biomaterial stained with (a) haematoxylin and eosin (b) Anti-CD3 (pan T-cell) and (c) Anti f4/80 (macrophage). Magnification is at ×40 and arrows indicate implanted biomaterials.
Figure 24:
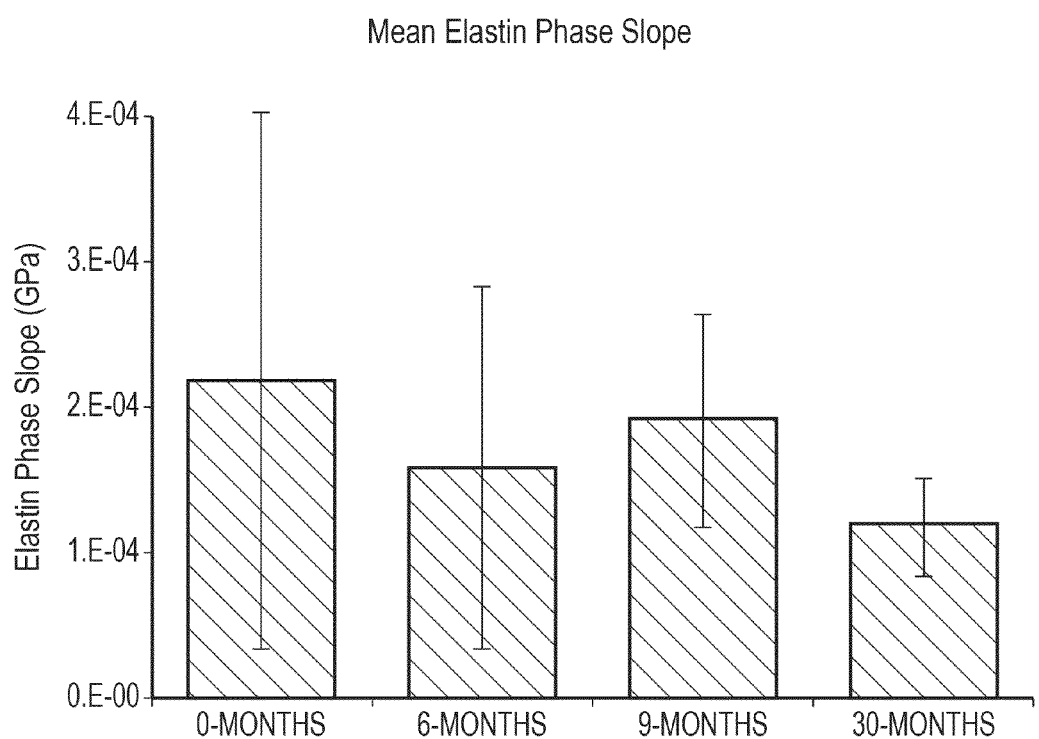
FIG. 24 shows a bar chart comparison representation of mean elastin phase slope between fresh decellularised bladder and decellularised bladder that has been stored for 6, 9 and 30 months respectively.
Figure 25:
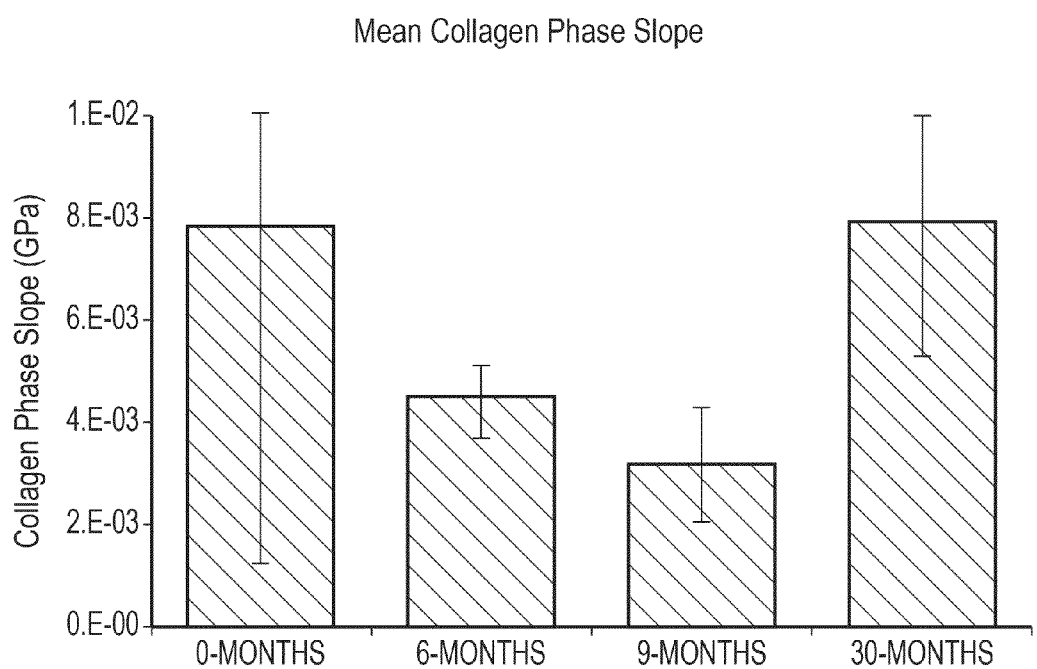
FIG. 25 shows a bar chart comparison representation of mean collagen phase slope between fresh decellularised bladder and decellularised bladder that has been stored for 6, 9 and 30 months respectively.
Figure 26:
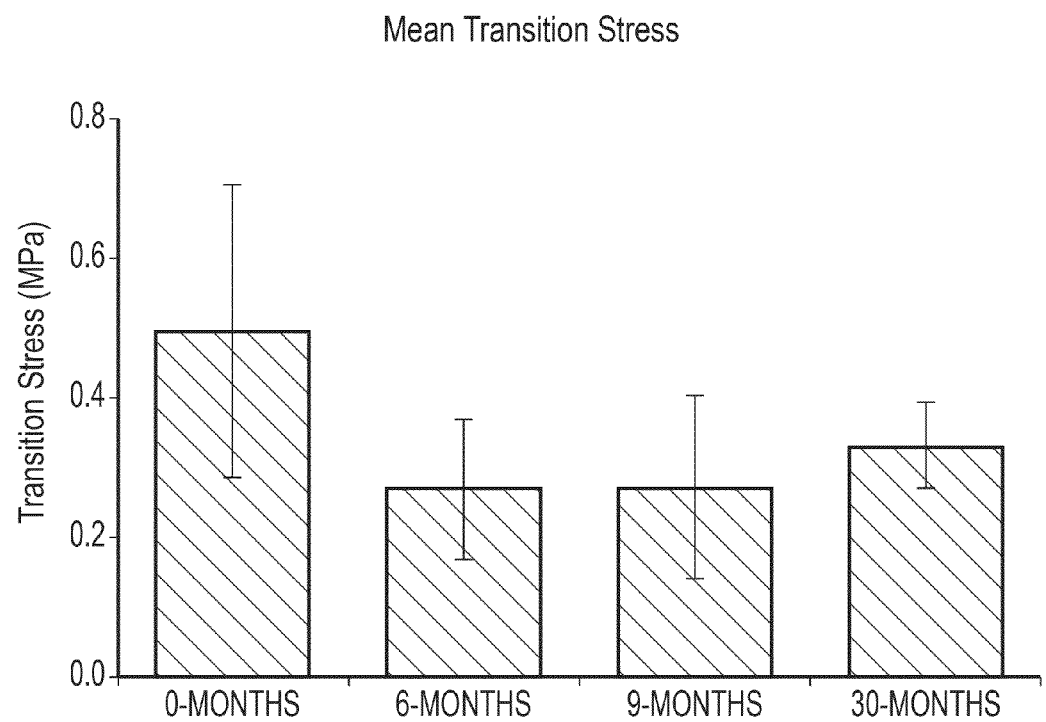
FIG. 26 shows a bar chart comparison representation of mean transition stress between fresh decellularised bladder and decellularised bladder that has been stored for 6, 9 and 30 months respectively.
Figure 27:
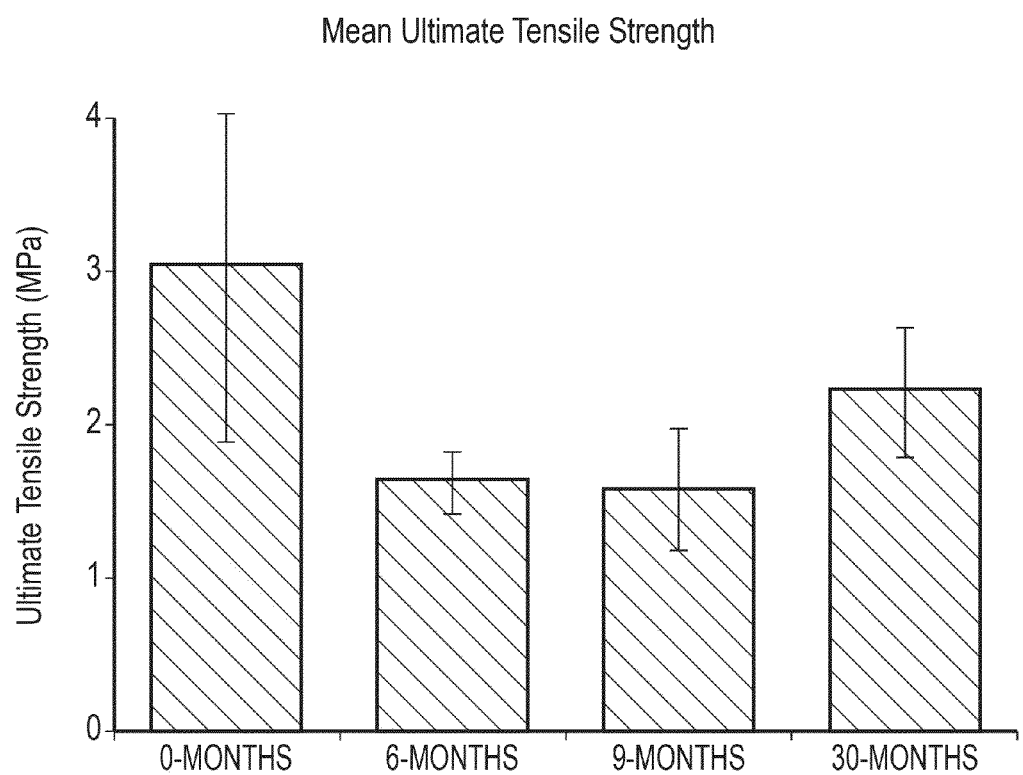
FIG. 27 shows a bar chart comparison representation of mean ultimate tensile strength between fresh decellularised bladder and decellularised bladder that has been stored for 6, 9 and 30 months respectively.
Figure 28:
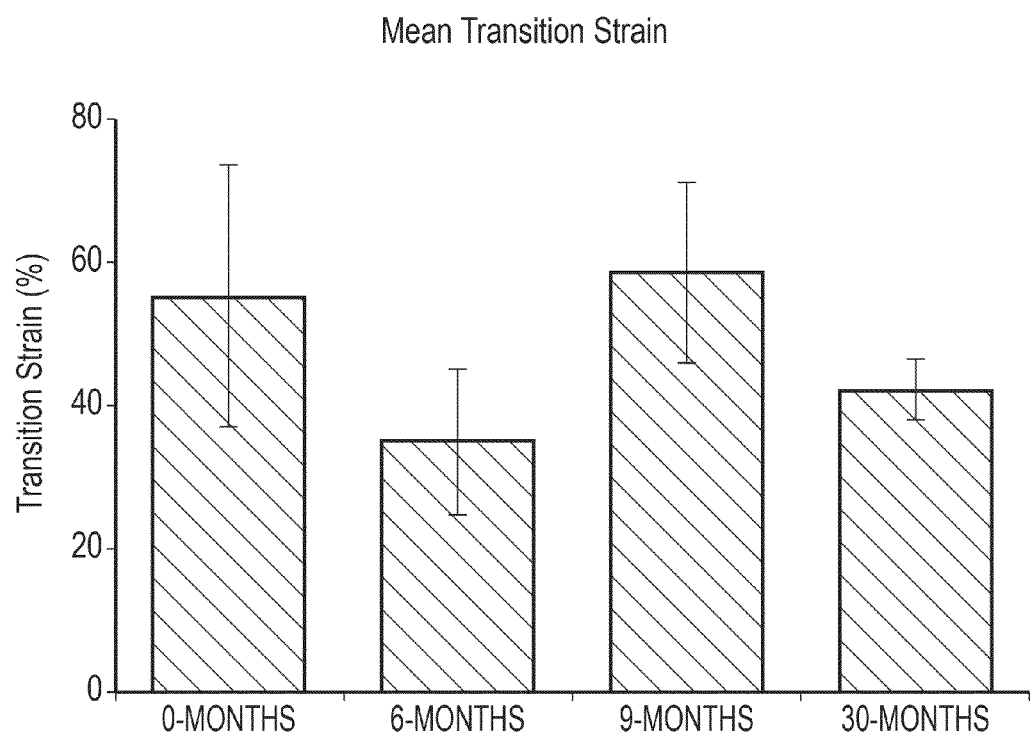
FIG. 28 shows a bar chart comparison representation of mean transition strength between fresh decellularised bladder and decellularised bladder that has been stored for 6, 9 and 30 months respectively.
Figure 29:
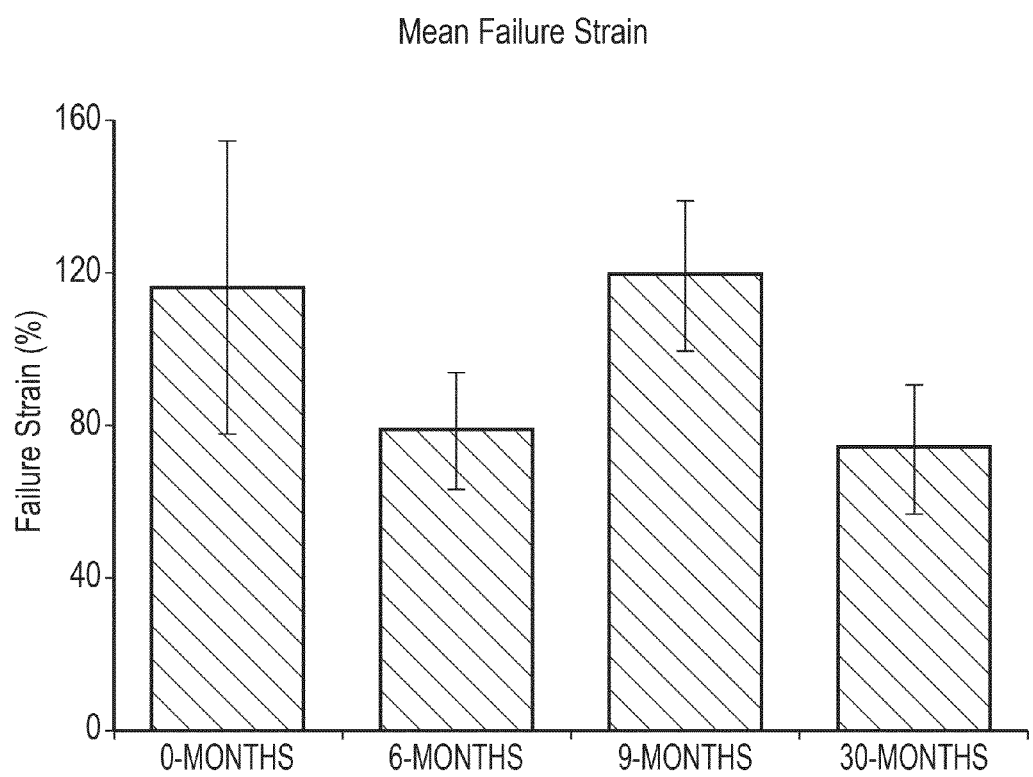
FIG. 29 shows a bar chart comparison representation of mean failure strength between fresh decellularised bladder and decellularised bladder that has been stored for 6, 9 and 30 months respectively.

The acellular porcine bladder biomaterial explants showed minimal encapsulation and the biomaterial appeared to be integrated into the mouse skin (FIG. 23). There were sparse CD3 positive T-cells around or within the biomaterial, although CD3 positive cells were clearly visible in the epidermis of the mouse skin (normal). There were signs of cellular infiltration into the matrix of the biomaterial, with some of these cells being F4/80 positive. Other cells had a fibroblastic appearance. The pattern was indicative of a wound healing-type reaction as judged by the presence of dispersed F4/80 positive cells in the absence of T-cells.

In contrast to the fresh bladder tissue which showed an overt foreign body response when implanted subcutaneously in mice, the acellular porcine bladder biomaterial showed good integration into the mouse skin indicating that the material was biocompatible in this model. This example provides evidence for the use of acellular porcine bladder biomaterials as appropriate material for wound healing.

Example 16

Aged stored samples of 6, 9, and 30 months old were tested for a variety of biomechanical strength parameters as hereinbefore described and compared to freshly (24 hour old) prepared decellularised bladder material. With references to FIGS. 24 to 29, there is presented bar chart results for mean elastin phase slope, collagen phase slope, transition stress, ultimate tensile strength, transition strain and failure strain respectively.

The results (Table 3) from uniaxial tensile testing indicated that there was no significant differences in any of the biomechanical parameters studied between decellularised scaffolds tested 24 hours post treatment and decellularised scaffolds tested 6, 9 and 30 months post treatment. P-values were calculated and obtained by ANOVA (Table 4).

These results indicate that the mechanical integrity of the decellularised bladder scaffolds remains intact for periods up to at least 30 months. In other words the shelf life of the material is at least 30 months.

TABLE 3

SELF LIFE STUDY

| | | DECELLULARISED BLADDER 0 MONTHS | | | | | (Lateral, Apex to Base) | | |
|---|---|---|---|---|---|---|---|---|---|
| Test No | E (GPa) | CoII-E (GPa) | $\sigma_T$ (MPa) | $\epsilon_T$ (%) | $\sigma_{UTS}$ (MPa) | $\epsilon_{UTS}$ (%) | Thick (mm) | Width (mm) | Length (mm) |
| 69 | 7.91E−05 | 5.04E−03 | 0.473 | 78.53 | 3.871 | 161.40 | 0.590 | 5.000 | 13.320 |
| 80 | 4.80E−04 | 1.60E−02 | 0.732 | 46.03 | 3.702 | 79.08 | 0.433 | 5.000 | 12.580 |
| 87 | 9.77E−05 | 2.51E−03 | 0.283 | 41.14 | 1.602 | 107.30 | 0.790 | 5.000 | 13.700 |
| Mean | 2.19E−04 | 7.85E−03 | 0.496 | 55.23 | 3.058 | 115.93 | 0.604 | | |
| StDev | 1.85E−04 | 5.85E−03 | 0.184 | 16.59 | 1.032 | 34.16 | 0.146 | | |
| Count | 3 | 3 | 3 | 3 | 3 | 3 | 3 | | |
| 95% C.I. | 2.09E−04 | 6.63E−03 | 0.208 | 18.78 | 1.168 | 38.65 | 0.165 | | |
| Test No | E (GPa) | CoII-E (GPa) | $\sigma_T$ (MPa) | $\epsilon_T$ (%) | $\sigma_{UTS}$ (MPa) | $\epsilon_{UTS}$ (%) | Thick (mm) | Width (mm) | Length (mm) |
| | | DECELLULARISED BLADDER 6 MONTHS | | | | | | | |
| 11 | 1.22E−04 | 3.74E−03 | 0.184 | 23.54 | 1.405 | 62.28 | 0.743 | 5.000 | 15.780 |
| 12 | 4.71E−05 | 4.31E−03 | 0.233 | 36.18 | 1.626 | 78.66 | 0.741 | 5.000 | 16.590 |
| 13 | 3.06E−04 | 5.24E−03 | 0.391 | 45.30 | 1.856 | 95.35 | 0.737 | 5.000 | 18.580 |
| Mean | 1.58E−04 | 4.43E−03 | 0.269 | 35.01 | 1.629 | 78.76 | 0.740 | | |
| StDev | 1.09E−04 | 6.18E−04 | 0.088 | 8.92 | 0.184 | 13.50 | 0.002 | | |
| Count | 3 | 3 | 3 | 3 | 3 | 3 | 3 | | |
| 95% C.I. | 1.23E−04 | 7.00E−04 | 0.100 | 10.10 | 0.208 | 15.28 | 0.003 | | |

TABLE 3-continued

SELF LIFE STUDY

DECELLULARISED BLADDER 9 MONTHS

| | | | | | | | | | |
|---|---|---|---|---|---|---|---|---|---|
| 8 | 1.22E−04 | 2.79E−03 | 0.142 | 43.18 | 1.334 | 97.20 | 0.862 | 5.000 | 15.370 |
| 9 | 1.76E−04 | 2.26E−03 | 0.248 | 67.82 | 1.299 | 139.50 | 0.870 | 5.000 | 13.240 |
| 10 | 2.76E−04 | 4.54E−03 | 0.425 | 65.44 | 2.088 | 122.10 | 0.874 | 5.000 | 14.470 |
| Mean | 1.91E−04 | 3.20E−03 | 0.272 | 58.81 | 1.574 | 119.60 | 0.869 | | |
| StDev | 6.36E−05 | 9.74E−04 | 0.117 | 11.10 | 0.364 | 17.36 | 0.005 | | |
| Count | 3 | 3 | 3 | 3 | 3 | 3 | 3 | | |
| 95% C.I. | 7.20E−05 | 1.10E−03 | 0.132 | 12.56 | 0.412 | 19.64 | 0.006 | | |

DECELLULARISED BLADDER 30 months

| | | | | | | | | | |
|---|---|---|---|---|---|---|---|---|---|
| 5 | 9.44E−05 | 1.10E−02 | 0.407 | 38.81 | 2.75 | 55.28 | 0.491 | 5.000 | 16.540 |
| 6 | 1.59E−04 | 7.04E−03 | 0.272 | 40.09 | 2.06 | 75.34 | 0.496 | 5.000 | 13.950 |
| 7 | 1.01E−04 | 5.63E−03 | 0.320 | 47.50 | 1.88 | 91.39 | 0.491 | 5.000 | 16.800 |
| Mean | 1.18E−04 | 7.89E−03 | 0.333 | 42.13 | 2.23 | 74.00 | 0.493 | | |
| StDev | 2.90E−05 | 2.27E−03 | 0.056 | 3.83 | 0.37 | 14.77 | 0.002 | | |
| Count | 3 | 3 | 3 | 3 | 3 | 3 | 3 | | |
| 95% C.I. | 3.28E−05 | 2.57E−03 | 0.063 | 4.33 | 0.42 | 16.72 | 0.003 | | |

TABLE 4

SELF LIFE ANOVA

| E (GPa) | | | | CoII-E (GPa) | | | |
|---|---|---|---|---|---|---|---|
| 0-MONTHS | 6-MONTHS | 9-MONTHS | 30-MONTHS | 0-MONTHS | 6-MONTHS | 9-MONTHS | 30-MONTHS |
| 7.91E−05 | 1.22E−04 | 1.22E−04 | 9.44E−05 | 5.04E−03 | 3.74E−03 | 2.79E−03 | 1.10E−02 |
| 4.80E−04 | 4.71E−05 | 1.76E−04 | 1.59E−04 | 1.60E−02 | 4.31E−03 | 2.26E−03 | 7.04E−03 |
| 9.77E−05 | 3.06E−04 | 2.76E−04 | 1.01E−04 | 2.51E−03 | 5.24E−03 | 4.54E−03 | 5.63E−03 |
| P-value | 0.710 | 0.850 | 0.488 | P-value | 0.457 | 0.330 | 0.993 |

| $\sigma_T$ (MPa) | | | | $\epsilon_T$ (%) | | | |
|---|---|---|---|---|---|---|---|
| 0-MONTHS | 6-MONTHS | 9-MONTHS | 30-MONTHS | 0-MONTHS | 6-MONTHS | 9-MONTHS | 30-MONTHS |
| 0.473 | 0.184 | 0.142 | 0.407 | 78.53 | 23.54 | 43.18 | 38.81 |
| 0.732 | 0.233 | 0.248 | 0.272 | 46.03 | 36.18 | 67.82 | 40.09 |
| 0.283 | 0.391 | 0.425 | 0.320 | 41.14 | 45.30 | 65.44 | 47.50 |
| P-value | 0.191 | 0.279 | 0.297 | P-value | 0.204 | 0.812 | 0.338 |

| $\sigma_{UTS}$ (MPa) | | | | $\epsilon_{UTS}$ (%) | | | |
|---|---|---|---|---|---|---|---|
| 0-MONTHS | 6-MONTHS | 9-MONTHS | 30-MONTHS | 0-MONTHS | 6-MONTHS | 9-MONTHS | 30-MONTHS |
| 3.871 | 1.405 | 1.334 | 2.747 | 161.40 | 62.28 | 97.20 | 55.28 |
| 3.702 | 1.626 | 1.299 | 2.061 | 79.08 | 78.66 | 139.50 | 75.34 |
| 3.602 | 1.856 | 2.088 | 1.883 | 107.30 | 95.35 | 122.10 | 91.39 |
| P-value | 0.126 | 0.127 | 0.346 | P-value | 0.226 | 0.899 | 0.186 |

The invention claimed is:

1. A method of implanting a tissue matrix in bladder reconstruction or replacement surgery comprising:
   immersing a distensible membranous sac in a buffer solution at a mild alkaline pH which includes active amounts of a proteolytic inhibitor;
   (ii) distending the distensible membranous sac by introducing a sufficient volume of the same buffer solution into the interior cavity of the sac;
   (iii) continuing decellularisation of the sac by replacing and introducing fresh solutions around the exterior surface of the sac and/or into the sac interior so as to maintain distension of the sac during recellularisation; and
   (iv) implanting the whole decellularised distensible sac or a portion thereof into a donor.

2. The method of claim 1 wherein steps (i) and (ii) are reversed.

3. The method of claim 1, wherein the distensible membranous sac is a whole bladder.

4. The method of claim 1, wherein the distensible membranous sac is derived from a pig or a human.

5. A method of urological tissue engineering replacement comprising:
   (i) immersing a bladder material in a buffer solution at a mild alkaline pH which includes a proteolytic inhibitor;
   (ii) expanding the bladder by introducing a sufficient volume of the same buffer solution into an interior cavity of the bladder so as to stretch and thin the bladder wall; and
   (iii) continuing decellularisation of the bladder by replacing and introducing fresh solutions both around the exterior surface of the bladder and into the bladder interior itself so as to maintain expansion of the bladder during decellularisation and to maintain the histoarchitecture of the bladder material; and
   (iv) implanting the bladder material or a portion thereof into a donor,
   wherein the method of tissue engineering replacement or tissue repair is selected from the group consisting of cosmetic surgery and scaffold for tissue-engineering.

* * * * *